(12) United States Patent
Benson et al.

(10) Patent No.: US 10,786,162 B2
(45) Date of Patent: Sep. 29, 2020

(54) VEHICLE SEAT WITH INTEGRATED SENSORS

(71) Applicant: Faurecia Automotive Seating, LLC, Auburn Hills, MI (US)

(72) Inventors: Matthew K. Benson, Holland, MI (US); Dana R. Lowell, Holland, MI (US); Sean M. Montgomery, Woodside, NY (US); Brian R. Dexter, Grand Haven, MI (US); Jeffery T. Bonk, Chesterfield, MI (US); David L. Cummings, Jackson Heights, NY (US); Alexander S. Haase, Ypsilanti, MI (US); Samuel Baudu, Boulogne Billancourt (FR); Radouane Boussetta, Massy (FR); Pioter Drubetskoy, Bronx New York, NY (US); Anne-Isabelle Dacosta-Mallet, Etrechy (FR)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 375 days.

(21) Appl. No.: 15/678,710

(22) Filed: Aug. 16, 2017

(65) Prior Publication Data
US 2017/0340214 A1 Nov. 30, 2017

Related U.S. Application Data

(63) Continuation of application No. 14/443,460, filed as application No. PCT/US2013/071620 on Nov. 25, 2013, now abandoned.
(Continued)

(51) Int. Cl.
*G08B 21/00* (2006.01)
*A61B 5/0205* (2006.01)
(Continued)

(52) U.S. Cl.
CPC ............ *A61B 5/0205* (2013.01); *A61B 5/021* (2013.01); *A61B 5/0245* (2013.01);
(Continued)

(58) Field of Classification Search
CPC ..... A61B 5/0205; A61B 5/021; A61B 5/0245; A61B 5/0402; A61B 5/0816;
(Continued)

(56) References Cited

U.S. PATENT DOCUMENTS

| | | | |
|---|---|---|---|
| 3,580,245 A | 5/1971 | Dill | |
| 4,031,579 A | 6/1977 | Larned | |

(Continued)

FOREIGN PATENT DOCUMENTS

| | | |
|---|---|---|
| CN | 1572575 | 2/2005 |
| CN | 1956680 A | 5/2007 |

(Continued)

OTHER PUBLICATIONS

Chinese Office Action for Chinese Pat. App. No. 201580011844.9 dated Jul. 12, 2019, 3619 CN II , 13 pages, (brief summary included in English).
(Continued)

*Primary Examiner* — Mark S Rushing
(74) *Attorney, Agent, or Firm* — Barnes & Thornburg LLP

(57) ABSTRACT

A vehicle seat in accordance with the present disclosure includes a seat bottom and a seat back. The seat back is coupled to the seat bottom and arranged to extend in an upward direction away from the seat bottom. The vehicle seat further includes an electronics system.

17 Claims, 15 Drawing Sheets

Related U.S. Application Data

(60) Provisional application No. 61/846,871, filed on Jul. 16, 2013, provisional application No. 61/730,349, filed on Nov. 27, 2012, provisional application No. 61/730,374, filed on Nov. 27, 2012.

(51) Int. Cl.
| | |
|---|---|
| *A61B 5/0245* | (2006.01) |
| *A61B 5/1455* | (2006.01) |
| *B60N 2/00* | (2006.01) |
| *A61B 5/00* | (2006.01) |
| *A61B 5/021* | (2006.01) |
| *A61B 5/0402* | (2006.01) |
| *A61B 5/08* | (2006.01) |
| *A61B 5/18* | (2006.01) |
| *B60H 1/00* | (2006.01) |

(52) U.S. Cl.
CPC .......... *A61B 5/0402* (2013.01); *A61B 5/0816* (2013.01); *A61B 5/14551* (2013.01); *A61B 5/14552* (2013.01); *A61B 5/18* (2013.01); *A61B 5/6893* (2013.01); *A61B 5/7278* (2013.01); *B60H 1/00742* (2013.01); *B60N 2/002* (2013.01)

(58) Field of Classification Search
CPC ... A61B 5/14551; A61B 5/14552; A61B 5/18; A61B 5/6893; A61B 5/7278; B60H 1/00742; B60N 2/002
USPC ...................................................... 340/573.1
See application file for complete search history.

(56) References Cited

U.S. PATENT DOCUMENTS

| | | | |
|---|---|---|---|
| 4,655,505 A | 4/1987 | Kashiwamura | |
| 4,707,027 A | 11/1987 | Horvath | |
| 4,840,425 A | 6/1989 | Noble | |
| 4,928,090 A * | 5/1990 | Yoshimi | A61B 5/18 340/575 |
| 5,069,214 A | 12/1991 | Samaras | |
| 5,155,685 A | 10/1992 | Kishi | |
| 5,462,515 A | 10/1995 | Tseng | |
| 6,055,473 A | 4/2000 | Zwolinski | |
| 6,212,719 B1 | 4/2001 | Thomas | |
| 6,273,810 B1 | 8/2001 | Rhodes, Jr. | |
| 6,422,087 B1 | 7/2002 | Potter | |
| 7,206,631 B2 | 4/2007 | Kawachi | |
| 7,239,945 B2 | 7/2007 | Hiemer | |
| 7,322,652 B1 | 1/2008 | Tache | |
| 7,774,052 B2 | 8/2010 | Burton | |
| 7,862,113 B2 | 1/2011 | Knoll | |
| 8,123,290 B1 | 2/2012 | Aiken | |
| 8,181,292 B1 | 5/2012 | Pellettiere | |
| 8,328,279 B2 | 12/2012 | Brncick | |
| 8,430,817 B1 | 4/2013 | Al-Ali | |
| 8,616,654 B2 | 12/2013 | Zenk | |
| 8,672,411 B2 | 3/2014 | Gomes | |
| 8,725,311 B1 | 5/2014 | Breed | |
| 8,757,726 B2 | 6/2014 | Oota | |
| 8,919,874 B2 | 12/2014 | Ota | |
| 9,135,803 B1 | 9/2015 | Fields | |
| 9,440,657 B1 | 9/2016 | Fields | |
| 9,475,389 B1 | 10/2016 | Fung | |
| 9,505,402 B1 | 11/2016 | Fung | |
| 9,717,345 B1 | 8/2017 | Caruso | |
| 9,848,814 B2 | 12/2017 | Benson | |
| 10,235,859 B1 | 3/2019 | Hiles | |
| 10,258,535 B2 | 4/2019 | Lem | |
| 10,471,864 B1 | 11/2019 | Tait | |
| 2002/0091473 A1* | 7/2002 | Gardner | G07C 5/0808 701/32.7 |
| 2004/0243368 A1* | 12/2004 | Hiemer | B60W 40/02 703/8 |
| 2005/0027416 A1 | 2/2005 | Basir | |
| 2005/0124864 A1 | 6/2005 | Mack | |
| 2005/0248184 A1 | 11/2005 | Piffaretti | |
| 2006/0025698 A1 | 2/2006 | Nakagawa | |
| 2006/0068693 A1 | 3/2006 | Kono | |
| 2006/0175877 A1 | 8/2006 | Alionte | |
| 2007/0029862 A1 | 2/2007 | Bargheer | |
| 2007/0251749 A1 | 11/2007 | Breed | |
| 2008/0296946 A1 | 12/2008 | Reynolds | |
| 2009/0030576 A1 | 1/2009 | Periot | |
| 2009/0164241 A1 | 6/2009 | Racioppo | |
| 2010/0185068 A1 | 7/2010 | Park | |
| 2010/0229181 A1 | 9/2010 | Ahuja | |
| 2011/0015468 A1 | 1/2011 | Aarts | |
| 2011/0066292 A1 | 3/2011 | Moriya | |
| 2011/0133755 A1 | 6/2011 | Griffin | |
| 2011/0156453 A1 | 6/2011 | Matsushima | |
| 2011/0186560 A1 | 8/2011 | Kennedy | |
| 2011/0304465 A1* | 12/2011 | Boult | B60K 28/06 340/576 |
| 2012/0078123 A1 | 3/2012 | Futatsuyama | |
| 2012/0212353 A1* | 8/2012 | Fung | B60W 30/08 340/905 |
| 2013/0070043 A1* | 3/2013 | Geva | B60K 28/066 348/14.02 |
| 2014/0031703 A1 | 1/2014 | Rayner | |
| 2014/0039330 A1 | 2/2014 | Seo Sang Man | |
| 2014/0228649 A1 | 8/2014 | Rayner | |
| 2014/0240132 A1 | 8/2014 | Bychkov | |
| 2014/0276112 A1 | 9/2014 | Fung | |
| 2015/0008710 A1 | 1/2015 | Young | |
| 2015/0051526 A1 | 2/2015 | Wang | |
| 2015/0151658 A1 | 6/2015 | Burris | |
| 2015/0231991 A1 | 8/2015 | Yetukuri | |
| 2015/0239321 A1 | 8/2015 | Müller | |
| 2015/0313475 A1 | 11/2015 | Benson | |
| 2016/0001781 A1 | 1/2016 | Fung | |
| 2016/0019813 A1 | 1/2016 | Mullen | |
| 2016/0029940 A1 | 2/2016 | Iizuka | |
| 2016/0086500 A1 | 3/2016 | Kaleal, III | |
| 2016/0339801 A1 | 11/2016 | Pereny | |
| 2016/0339802 A1 | 11/2016 | Hanlon | |
| 2017/0136842 A1 | 5/2017 | Anderson | |
| 2017/0136922 A1 | 5/2017 | Von Ballmoos | |
| 2017/0158202 A1 | 6/2017 | Yang | |
| 2017/0282930 A1 | 10/2017 | Kochhar | |
| 2017/0285641 A1 | 10/2017 | Goldman-Shenhar | |
| 2017/0312534 A1 | 11/2017 | Cao | |
| 2017/0326013 A1 | 11/2017 | Hyde | |
| 2017/0340214 A1 | 11/2017 | Benson | |
| 2018/0037236 A1 | 2/2018 | Yamaguchi | |
| 2018/0178808 A1 | 6/2018 | Zhao | |
| 2018/0229674 A1 | 8/2018 | Heinrich | |

FOREIGN PATENT DOCUMENTS

| | | |
|---|---|---|
| CN | 103565429 A | 2/2014 |
| CN | 104837403 A | 8/2015 |
| CN | 0104875744 | 9/2015 |
| DE | 102005038289 | 3/2007 |
| DE | 102007053119 | 5/2009 |
| DE | 102009021532 | 11/2010 |
| EP | 1447070 A | 8/2004 |
| JP | 2010264092 | 11/2010 |
| KR | 1020010061858 | 7/2001 |
| KR | 1020140027641 | 3/2014 |
| KR | 0101642697 | 8/2016 |
| WO | 2013109154 | 7/2013 |
| WO | 2013109154 A1 | 7/2013 |
| WO | 02014147828 | 9/2014 |
| WO | 2014147828 | 9/2014 |
| WO | 2015127193 | 8/2015 |

(56) References Cited

FOREIGN PATENT DOCUMENTS

| WO | 2015200224 | 12/2015 |
| WO | 2016070981 | 5/2016 |

OTHER PUBLICATIONS

European Examination Report for European App. No. 15 707 235.6 dated Feb. 6, 2018, 3619 EP ‖ , 7 pages.
Chinese Office Action for Chinese App. No. 201380064313.2 dated Apr. 12, 2017, 3376 CN ‖ , 21 pages.
Chinese Office Action for Chinese App. No. 201380064313.2 dated Sep. 28, 2017, 3376 CN ‖ , 19 pages.
PCT International Search Report and Written Opinion completed by the ISA/US dated Apr. 22, 2014 and issued in connection with PCT/US2013/071620.
PCT Search Report and Written Opinion completed by the ISA/EP dated May 21, 2015 and issued in connection with PCT/US2015/016803, 13 pages.
Office Action dated Nov. 29, 2017 for U.S. Appl. No. 15/235,882; ‖ , (pp. 1-7).
Chinese Rejection Decision for Chinese App. No. 201380064313.2 dated May 17, 2018, 3376 CN ‖ , 13 pages.
Chinese Office Action for Chinese Pat. App. No. 201580011844.9 dated Mar. 14, 2019, 3619 CN ‖ , 12 pages, (brief summary included in English).
Office Action dated May 1, 2019 for U.S. Appl. No. 15/692,396, 4112 US-U ‖ (pp. 1-27).
Office Action dated May 16, 2019 for U.S. Appl. No. 15/626,525, 4081 US-U ‖ (pp. 1-12).
Chinese Office Action for Chinese App. No. 201710799929.9 dated Sep. 27, 2019, 4112 CN ‖ , 14 pages.
Office Action dated Oct. 29, 2019 for U.S. Appl. No. 15/692,396, 4112 US-U ‖ (pp. 1-37).
Chinese Office Action for Chinese Pat. App. No. 201580011844.9 dated Nov. 19, 2019, 3619 CN ‖ , 13 pages, (brief summary included in English).
Chinese Office Action for Chinese Pat. App. No. 201580011844.9 dated Aug. 28, 2018, 3619 CN ‖ , 19 pages, (brief summary included in English).
Office Action dated Sep. 3, 2019 for U.S. Appl. No. 15/613,578, 4078 US-U ‖ , (pp. 1-20).
Fifth Chinese Office Action for Chinese Pat. App. No. 201580011844.9 dated Mar. 13, 2020, 3619 CN ‖ , 13 pages, (brief summary included in English).
Choi et al., "Noninvaisive cuffless blood pressure estimation usingpulse transit time and Hilbert-Huang transform," Computers and Electridal Engineering Journal, 39, 103-111 (Nov. 8, 2012), 9 pages.
Wong et al., "The Effects of Exercises on teh Relationship between Pulse Transit Time and Arterial Blood Pressure," Proceedings of the 2005 IEEE Enginering in Medicine and Biology 27th Annual Conference, Shanghai, China , Sep. 1-4, 2005, 3 pages.
Office Action dated Apr. 27, 2020 for U.S. Appl. No. 15/626,525, 4081 US-U ‖ (pp. 1-11).
Office Action dated Apr. 30, 2020 for U.S. Appl. No. 15/873,034, 4296 US-U ‖ (pp. 1-24).
European Examination Report for European App. No. 15 707 235.6 dated Apr. 15, 2020, 3619 EP ‖ , 5 pages.
Office Action dated Apr. 30, 2020 for U.S. Appl. No. 15/863,129, 4296 US-U ‖ (pp. 1-23).
Office Action dated May 8, 2020 for U.S. Appl. No. 15/613,578, 4078 US-U ‖ (pp. 1-23).
N. Mizuno and K. Washino, "A model based filtering technique for driver's heart rate monitoring using seat-embedded vibration sensors," 2014 6th International Symposium on Communications, Control and Signal Processing (ISCCSP), Athens, 2014, pp. 137-140, doi: 10.1109/ISCCSP.2014.6877834. (Year: 2014).
Second Chinese Office Action for Chinese App. No. 201710799929.9 dated Jul. 1, 2020, 4112 CN ‖ 6 pages.

* cited by examiner

| Pulse Ox Sensor | Description | Manufacturer | Part Number |
|---|---|---|---|
| | PHOTODIODE PIN HI SPEED HI SENS w DL Filter | | VBPW34FAS |
| | OPA2277 | TI | OPA2277UA |
| | 10K Res | Yageo | RC0603FR-0710KL |
| | 100K Res | Yageo | RC0603FR-07100KL |
| | 0.47nF Cap | TDK | C1608C0G1H471F |
| | 1050nm LED | Epitex | SMT1050 |
| | 950nm LED | Vishay | VSMS3700-GS08 |
| | 850nm LED | Vishay | VSMY3850-GS08 |
| | 830nm LED | Vishay | VSMG2700-GS08 |
| | 810nm LED | Epitex | SMT810N |
| | Inverter Logic Gate | | SN74LVC1GU04DCKR |
| | AND Gate | | SN74LVC1G08DCKR |
| | MIC4812 | Micrel | MIC4812YMME |
| | 8.45K SET Res | Vishay | CRCW06038K45FKEA |
| | 200K Res | Vishay | CRCW0603200KFKEA |
| | 2.2uF Cap | Murata | GRM188R60J225KE19D |
| | 22uF Cap | TDK | C1608X5R0J226M |
| | 0.1uF Cap | Murata | GRM188R71C104KA01D |
| | CONN RCPT 7POS 1.25MM R/A SMD | Molex | 5023860770 |
| | CONN RCPT 7POS 1.25MM W/B VERT | Molex | 5023820770 |
| | CONN PLUG HSNG 7POS 1.25MM WTB | Molex | 5023800700 |
| Pulse Ox Extras | PLUG TERM 1.25 26-28AWG TIN | Molex | 5023810000 |
| | 8.25K Res | | CRCW06038K25FKEA |
| | PHOTODIODE PIN HI SPEED HI SENS w/o DL Filter | | VBPW34S |
| | 0603 Resistor Kit | | PHG2A-KIT |
| | 0603 Cap Kit 10pF-0.1uF | | S-0603-DIGI |
| | OR gate | TI | SN74LVC1G32DCKR |

*FIG. 19*

VEHICLE SEAT WITH INTEGRATED SENSORS

PRIORITY CLAIM

This application is a U.S. continuation application of U.S. patent application Ser. No. 14/443,460 filed May 18, 2015, which is a U.S. national counterpart application of International Application Serial No. PCT/US2013/071620 filed Nov. 25, 2013, which claims the benefit of U.S. Provisional Patent Application No. 61/846,871 filed Jul. 16, 2013, U.S. Provisional Patent Application No. 61/730,349 filed Nov. 27, 2012, and U.S. Provisional Patent Application No. 61/730,374 filed Nov. 27, 2012, each of which is expressly incorporated by reference herein.

BACKGROUND

The present disclosure relates to a vehicle seat, and particular to a vehicle seat including a sensor. More particularly, the present disclosure relates to a vehicle seat including one or more sensors configured to sense a physiological attribute, condition and/or state of an occupant sitting on the vehicle seat.

SUMMARY

A vehicle seat in accordance with the present disclosure includes a seat bottom and a seat back. The seat back is coupled to the seat bottom and arranged to extend in an upward direction away from the seat bottom. In one illustrative embodiment, the vehicle seat further includes an electronics system.

In illustrative embodiments, the electronics system is configured to provide means for sensing a physiological attribute of an occupant sitting on the vehicle seat through clothing worn by the occupant so that a predetermined action may be taken in response to the physiological attribute detected by the electronics system.

In other illustrative embodiments, the electronics system includes an electrocardiogram (ECG) system. The ECG system is coupled to the vehicle seat to sense electrical signals in the occupant through the occupant's clothing and covert the electrical signals to a heart rate of the occupant. In other illustrative embodiments, the electronics system includes an oximetry system. The oximetry system is coupled to the seat bottom to sense oxygen in the occupant's blood through the occupant's clothing and convert the sensed oxygen content into a respiration rate.

In illustrative embodiments, a vehicle seat sensor system for detecting and processing physiological parameters is disclosed, where the system comprises a vehicle seat, configured to accommodate an occupant, at least one oxymetry sensor integrated into a first portion of the seat, wherein the oxymetry sensor is configured to switch between, or select from, multiple wavelengths of light for transmission to an occupant area above a surface of the vehicle seat. The system also comprises a control system operatively coupled to the oxymetry sensor, wherein the control system processes signals produced by the at least one oxymetry sensor to determine a level of oxygen saturation for the occupant. The system may be configured such that the level of oxygen saturation is processed to determine at least one of a pulse transit time, blood pressure, respiration, respiration rate and respiration depth of the occupant. The vehicle sensor system may further include at least one electrocardiogram (ECG) sensor integrated into a second portion of the vehicle seat, wherein the ECG sensor is operatively coupled to the control system. The control system may be configured to processes signals produced by the ECG sensor to determine at least one of heart rate, heart rate variability, stress level, a pulse-transit time and blood pressure of the occupant.

In illustrative embodiments, a method is disclosed for detecting and processing physiological parameters from a vehicle seat sensor system, where the method includes the steps of configuring at least one oxymetry sensor, integrated into a first portion of a vehicle seat to switch between, or select from, multiple wavelengths of light for transmission to an occupant area above a surface of the vehicle seat. After receiving signals from the at least one oxymetry sensor, a level of oxygen saturation is detected in a control system for the occupant in the vehicle seat. The method may further include the steps of processing the detected levels of oxygen saturation in a control system to determine at least one of a pulse transit time, blood pressure, respiration, respiration rate and respiration depth of the occupant. At least one electrocardiogram (ECG) sensor may also be integrated into a second portion of the vehicle seat to receive electrical signals from the occupant, wherein the control system processes the ECG signals to determine at least one of a heart rate, heart rate variability, stress level, a pulse-transit time and blood pressure of the occupant.

In illustrative embodiments, a vehicle seat sensor system for detecting and processing physiological parameters, comprises a vehicle seat, configured to accommodate an occupant, at least one oxymetry sensor integrated into a first portion of said seat, wherein the oxymetry sensor is configured to switch between, or select from, multiple wavelengths of light for transmission to an occupant area above a surface of the vehicle seat, and a control system operatively coupled to the oxymetry sensor, wherein the control system processes signals produced by the at least one oxymetry sensor to determine a level of oxygen saturation for the occupant.

According to a further embodiment of the present disclosure, the level of oxygen saturation is processed to determine at least one of a pulse transit time, blood pressure, respiration, respiration rate and respiration depth of the occupant.

According to a further embodiment of the present disclosure, the oxymetry sensor comprises a photodetector stage configured to detect reflected amounts of light from the occupant, a processing stage, operatively coupled to the photodetector stage, for processing signals detected by the photodetector stage, wherein at least a portion of the processed signals are used to switch or select one or more of the multiple wavelengths of light for transmission, and a light emission stage, operatively coupled to the processing stage, configured to emit light for transmission to the occupant area.

According to a further embodiment of the present disclosure, the processing stage is configured to cycle and perform spectral analysis on at least some of the multiple wavelengths of light to determine at least one optimal wavelength for determining the level of oxygen saturation.

According to a further embodiment of the present disclosure, the light emission stage comprises at least one LED bank operable in the 850 nm to 950 nm light range.

According to a further embodiment of the present disclosure, the light emission stage further comprises at least one LED bank operable in the 600 nm to 1100 nm light range.

According to a further embodiment of the present disclosure, the control system is configured to process signals by transforming and filtering electrical signals received from the occupant.

According to a further embodiment of the present disclosure, the vehicle seat sensor system further comprises at least one electrocardiogram (ECG) sensor integrated into a second portion of said seat, wherein the ECG sensor is operatively coupled to the control system.

According to a further embodiment of the present disclosure, the control system processes signals produced by the ECG sensor to determine at least one of a heart rate, heart rate variability, stress level, a pulse-transit time and blood pressure of the occupant.

According to a further embodiment of the present disclosure, the control system is configured to determine heart beats via threshold and peak detection of the signals produced by the ECG sensor.

According to a further embodiment of the present disclosure, the control system is configured to determine the reliability of signals produced by the ECG sensor by performing at least one of peak analysis to the outputs, root mean square of outputs to determine stronger signals, and signal to noise ratio analysis on the outputs to determine more reliable signals.

According to a further embodiment of the present disclosure, the control system is configured to determine heart-rate variability by transforming signals produced by the ECG sensor to form a heart rate variability spectrum and determining a ratio of high frequencies to lower frequencies in the spectrum.

According to a further embodiment of the present disclosure, the ratio of high frequencies to lower frequencies is expressed by $$\frac{LF}{(LF+HF)}.$$

According to a further embodiment of the present disclosure, the control system is configured to determine a stress level based on a second ratio of high frequencies to lower frequencies in the spectrum.

According to a further embodiment of the present disclosure, the second ratio of high frequencies to lower frequencies is expressed by $$\sqrt{\frac{LF}{(LF+HF)}}.$$

According to a further embodiment of the present disclosure, the control system is configured to combine the signals produced by the ECG sensor and oximetry sensor to determine a pulse-transit time and blood pressure.

In illustrative embodiments, a method for detecting and processing physiological parameters from a vehicle seat sensor system comprises the steps of configuring at least one oxymetry sensor, integrated into a first portion of a vehicle seat to switch between, or select from, multiple wavelengths of light for transmission to an occupant area above a surface of the vehicle seat, receiving signals from said at least one oxymetry sensor, and detecting a level of oxygen saturation in a control system for the occupant in the vehicle seat based on the received signals.

According to a further embodiment of the present disclosure, the step of processing the detected levels of oxygen saturation in a control system to determine at least one of a pulse transit time, blood pressure, respiration, respiration rate and respiration depth of the occupant.

According to a further embodiment of the present disclosure, the method further comprises the steps of configuring at least one electrocardiogram (ECG) sensor integrated into a second portion of said vehicle seat to receive electrical signals from said occupant and receiving signals from said at least one ECG sensor.

According to a further embodiment of the present disclosure, the method further comprises the step of processing the received signals from the ECG sensor in a control system to determine at least one of a heart rate, heart rate variability, stress level, a pulse-transit time and blood pressure of the occupant.

In illustrative embodiments, a method for detecting and processing physiological parameters, from a vehicle seat sensor system, comprises the steps of configuring at least one oxymetry sensor, integrated into a first portion of a vehicle seat to switch between, or select from, multiple wavelengths of light for transmission to an occupant area above a surface of a vehicle seat, receiving signals from said at least one oxymetry sensor, configuring at least one electrocardiogram (ECG) sensor integrated into a second portion of said vehicle seat to receive electrical signals from said occupant, receiving signals from said at least one ECG sensor, and processing the received signals from the at least one oxymetry sensor and at least one ECG sensor in a control system to determine (i) a level of oxygen saturation for the occupant, and/or (ii) at least one of a heart rate, heart rate variability, stress level, a pulse-transit time and blood pressure of the occupant.

In illustrative embodiments, a vehicle seat comprises a seat bottom, a seat back coupled to the seat bottom and arranged to extend in an upward direction away from the seat bottom, and an electronics system configured to provide means for sensing a physiological attribute of an occupant sitting on the vehicle seat through clothing worn by the occupant so that a predetermined action may be taken in response to the physiological attribute detected by the electronics system.

According to a further embodiment of the present disclosure, the electronics system includes an electrocardiogram (ECG) system coupled to the vehicle seat to sense electrical signals in the occupant through the occupant's clothing and covert the electrical signals to a heart rate of the occupant.

According to a further embodiment of the present disclosure, the ECG system is coupled to the seat back and configured to sense electrical signals through a torso included in the occupant.

According to a further embodiment of the present disclosure, the electronics system further includes an oximetry system coupled to the vehicle seat to sense oxygen in the occupant's blood through the occupant's clothing and convert the sensed oxygen content into a respiration rate.

According to a further embodiment of the present disclosure, the oximetry system is coupled to the seat bottom and configured to sense oxygen in the occupant's blood through legs included in the occupant.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The present disclosure will be better understood and other features and advantages will become apparent upon reading the following detailed description, including embodiments as non-limiting particular examples with reference to the attached drawings, can be used to complete the understanding of the present disclosure, its implementation and, where appropriate, contribute to its definition, in which FIG. 1 is a perspective and diagrammatic view of a vehicle seat in accordance with the present disclosure illustrating an exemplary vehicle seat that includes a seat bottom supporting two oximetry sensors that sense an amount of oxygen in an occupant's blood through the occupant's clothing to provide an oximetry signal, a seat back supporting a plurality of electrocardiogram (ECG) receivers that cooperate with an ECG mat included in the seat bottom to sense electrical signals in the occupant through the occupant's clothing to provide an ECG signal, and a computer that receives the signals and processes the signals to provide a measured heart rate, blood pressure, respiration, and stress information;

FIG. 1A is an illustration of another embodiment of a vehicle seat in accordance with the present disclosure showing that a first oximetry sensor is spaced apart a first distance from a front edge of a seat bottom included in the vehicle seat and that a second oximetry is spaced apart from the front edge relatively smaller second distance so that contact by the occupant with the oximetry sensors is maximized;

FIG. 2 is a diagrammatic view of the seat back of FIG. 1 showing that the seat back includes a seat cushion and trim surrounding the seat cushion and that the ECG sensor is coupled to the seat back to lie in confronting relation with an occupant wearing multiple layers of clothing and suggesting that the ECG sensor is capable of sensing the occupant's electrical signals through the multiple layers of clothing;

FIG. 3 is a diagrammatic view of a portion of the seat bottom of FIG. 1 showing that the seat bottom includes a seat cushion and trim surrounding the seat cushion and that the oximetry sensor is coupled to the seat bottom to lie in confronting relation with the occupant wearing multiple layers of clothing and suggesting that the oximetry sensor is capable of sensing the oxygen content of the occupant's blood through the multiple layers of clothing;

Figure 1:
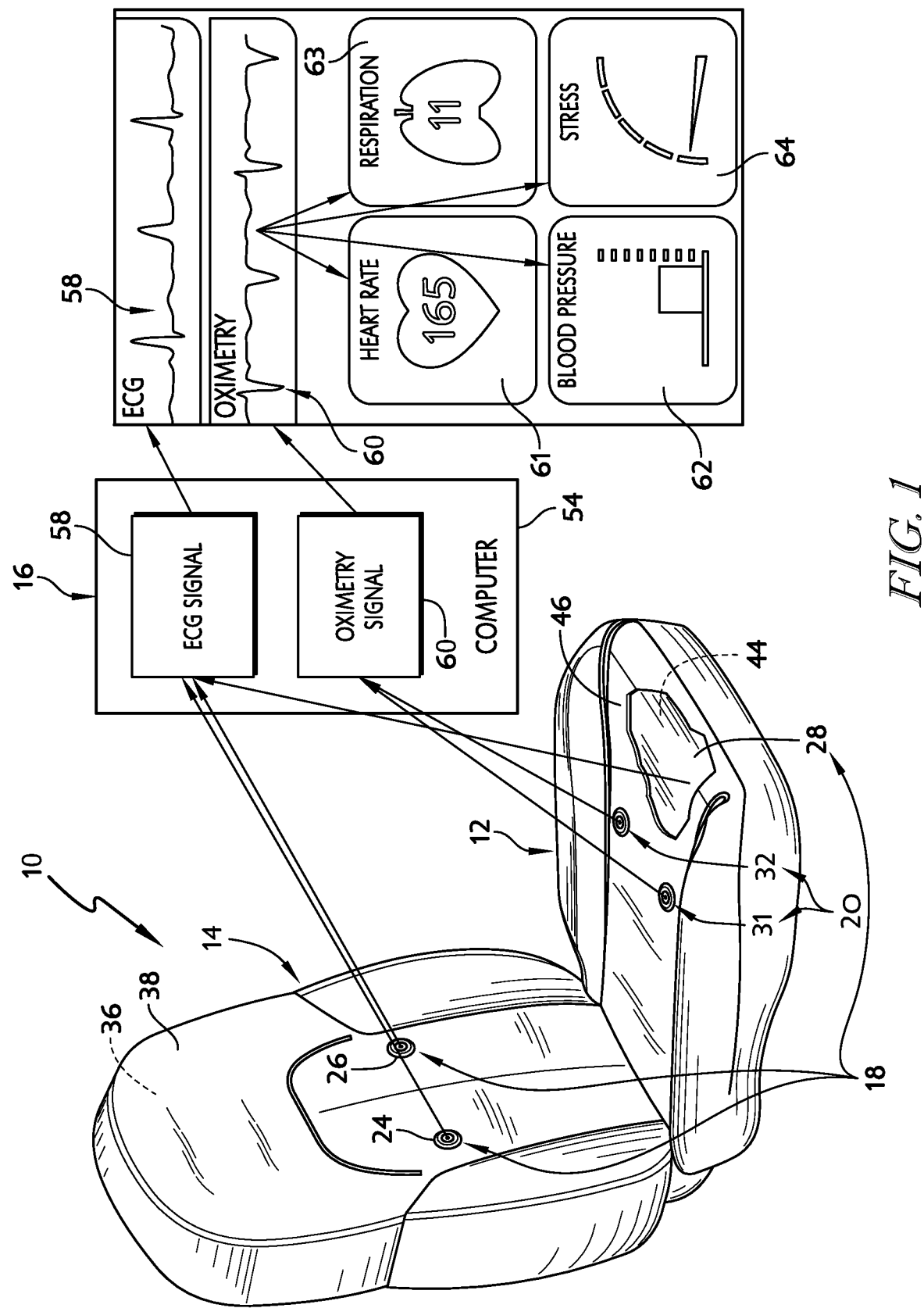
Figure 1A:
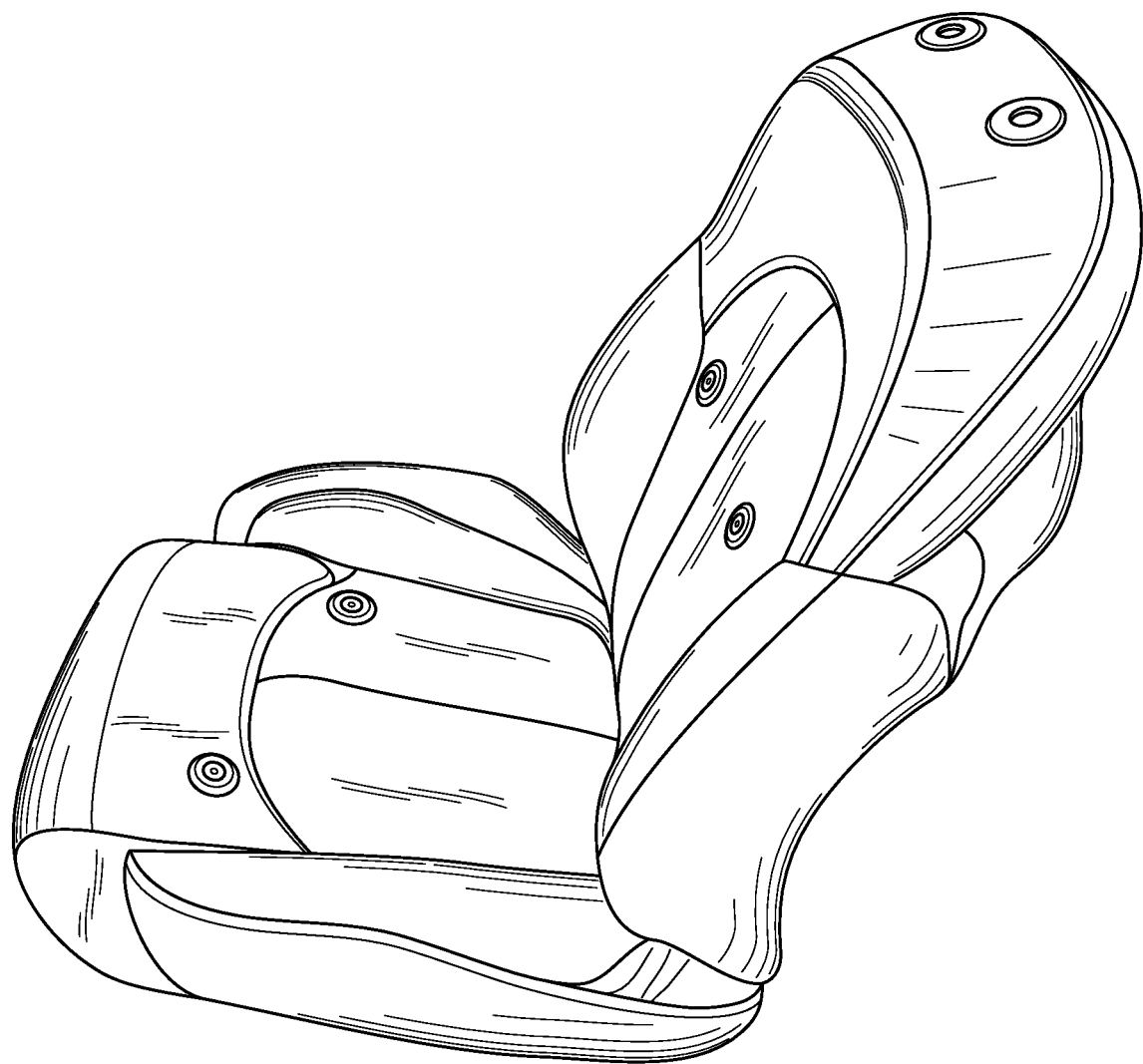
Figure 8:
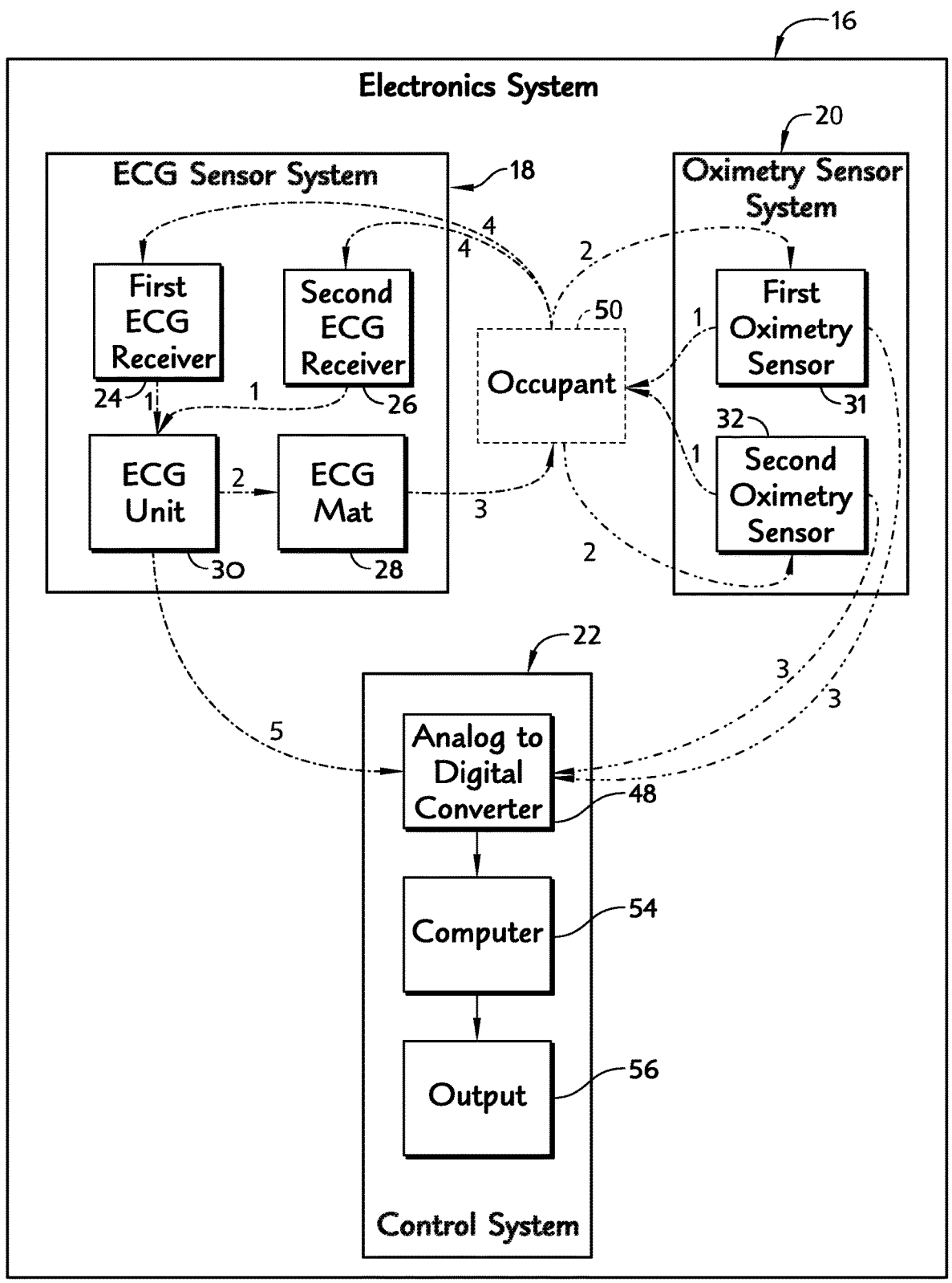
Figure 9:
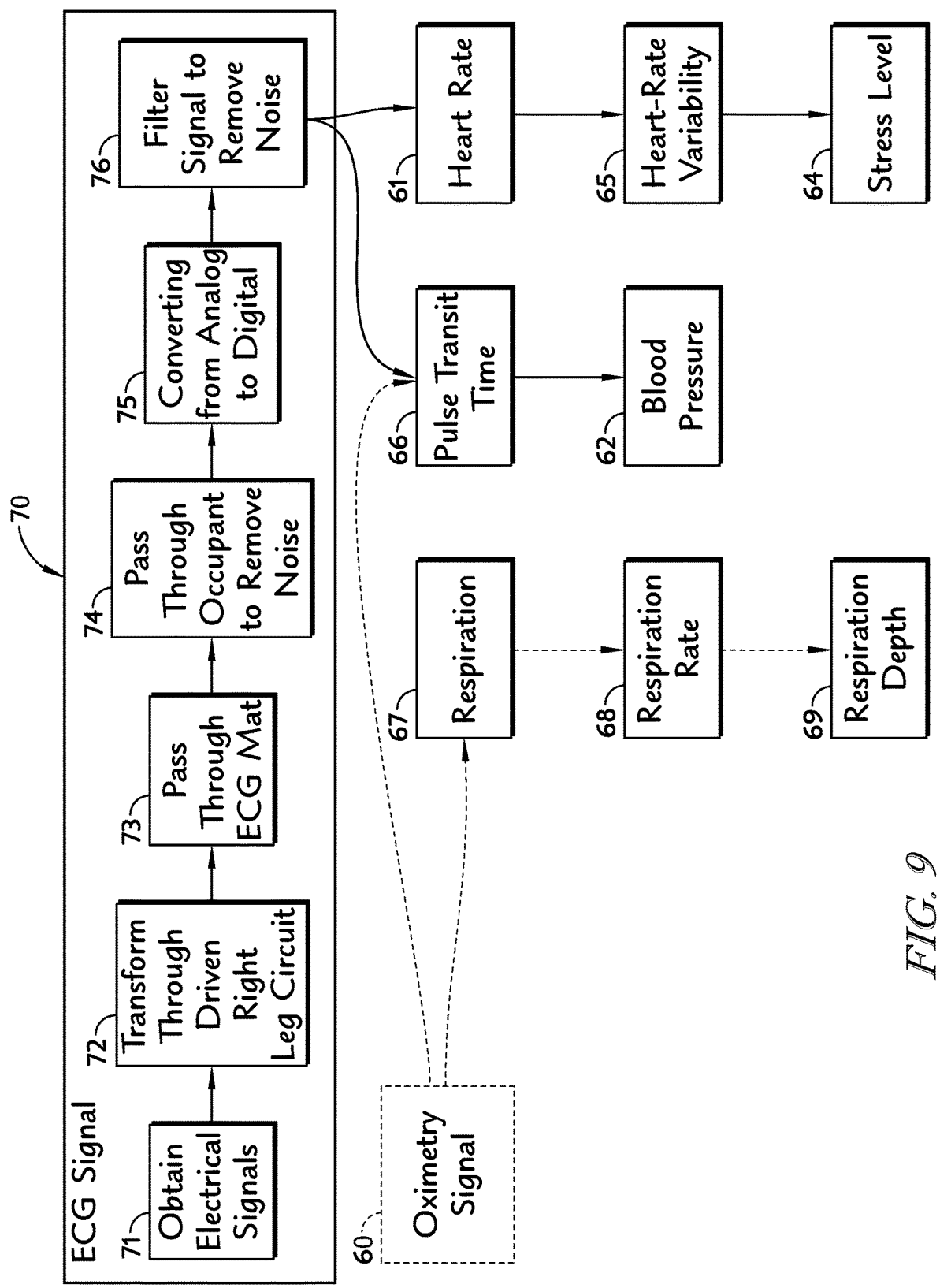
Figure 10:
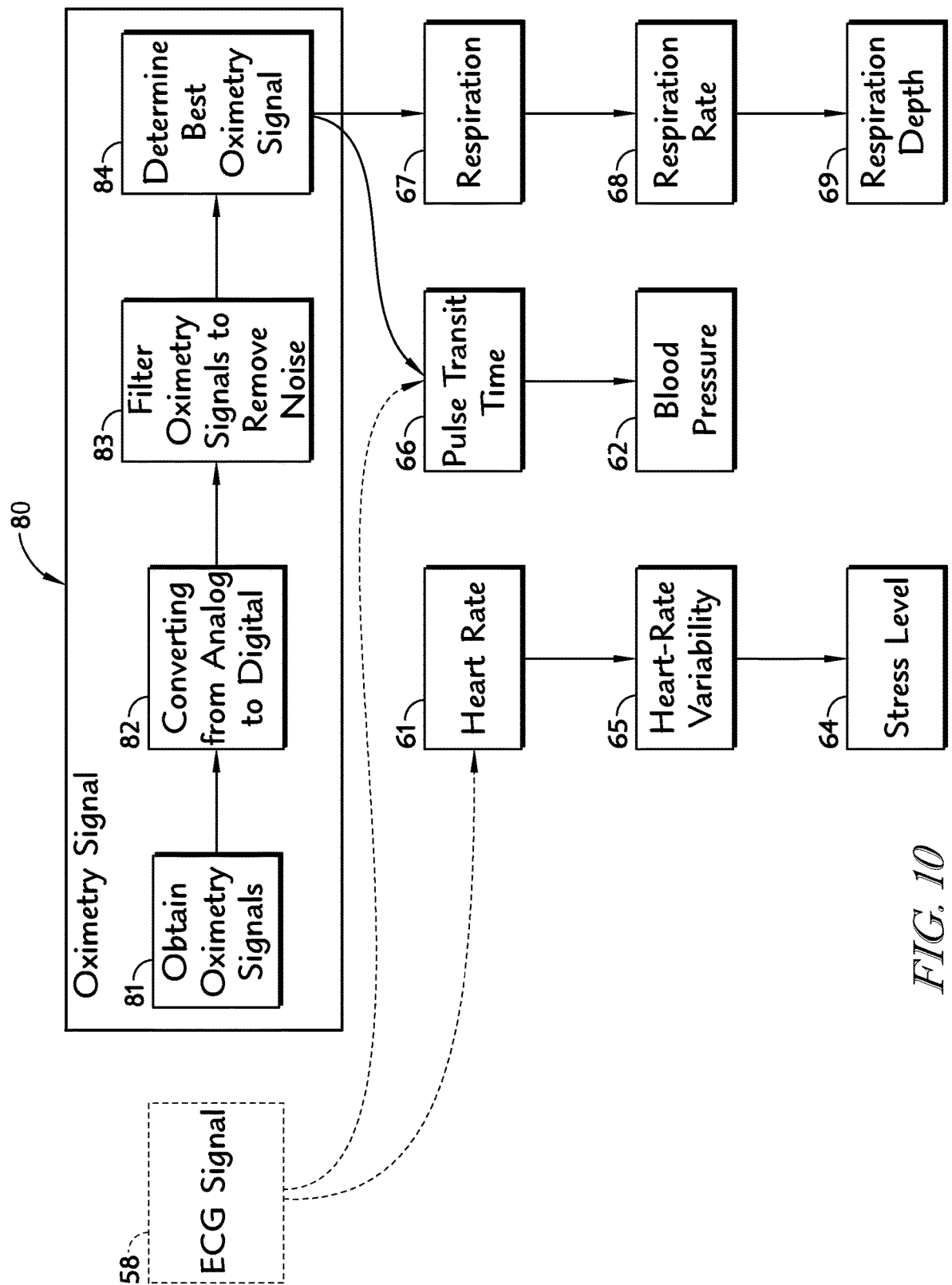
Figure 11:
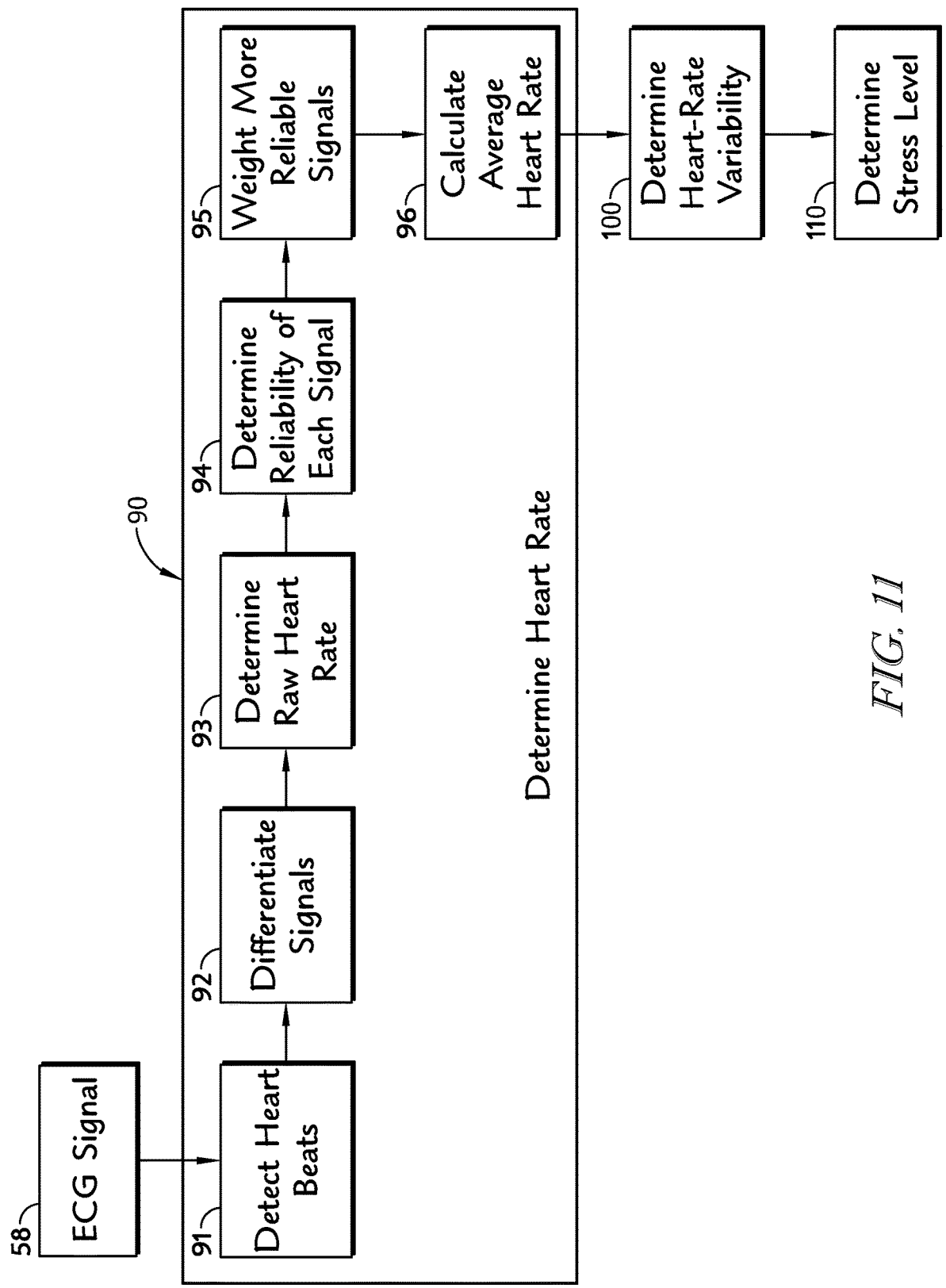
Figure 12:
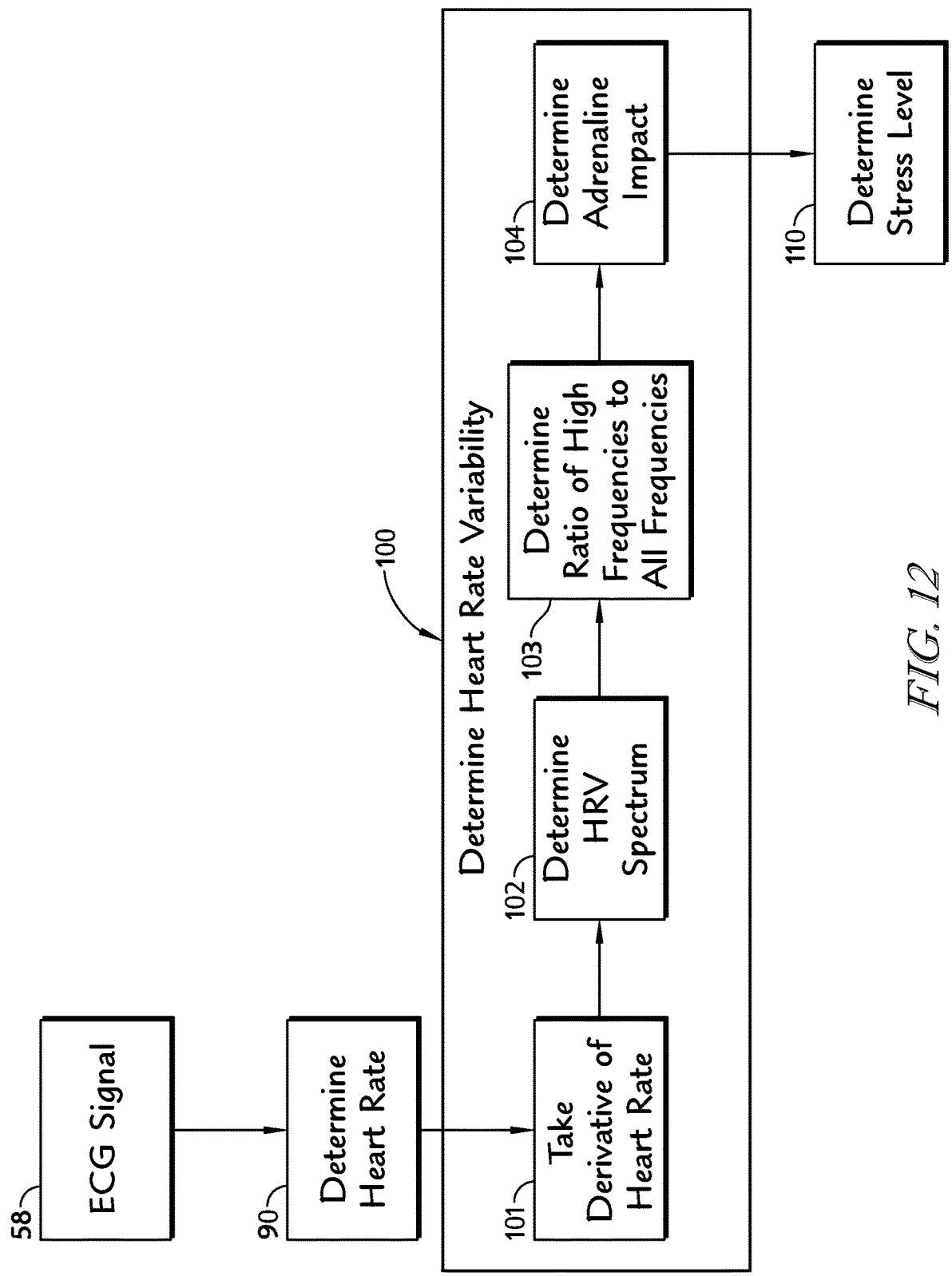
Figure 13:
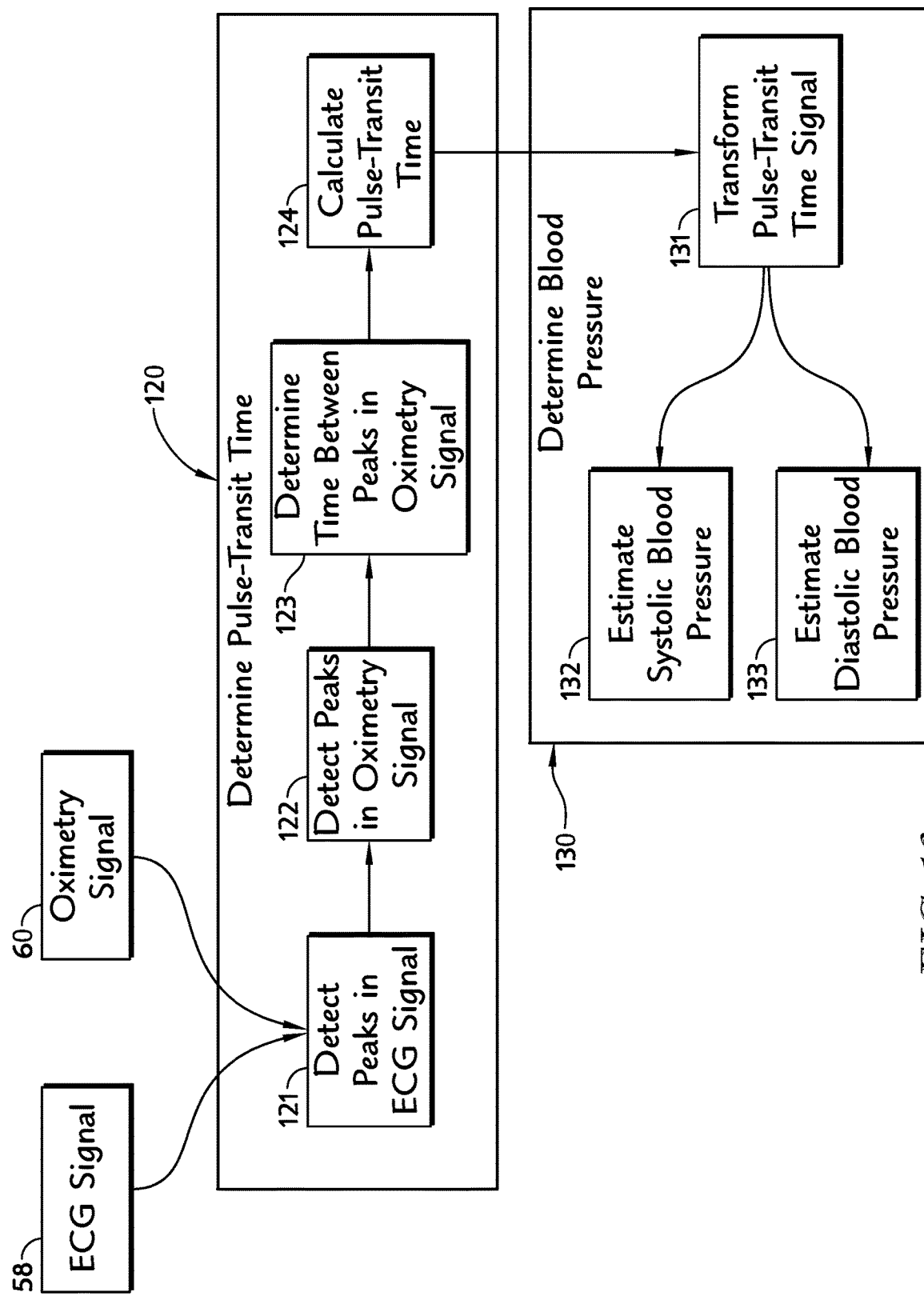
Figure 14:
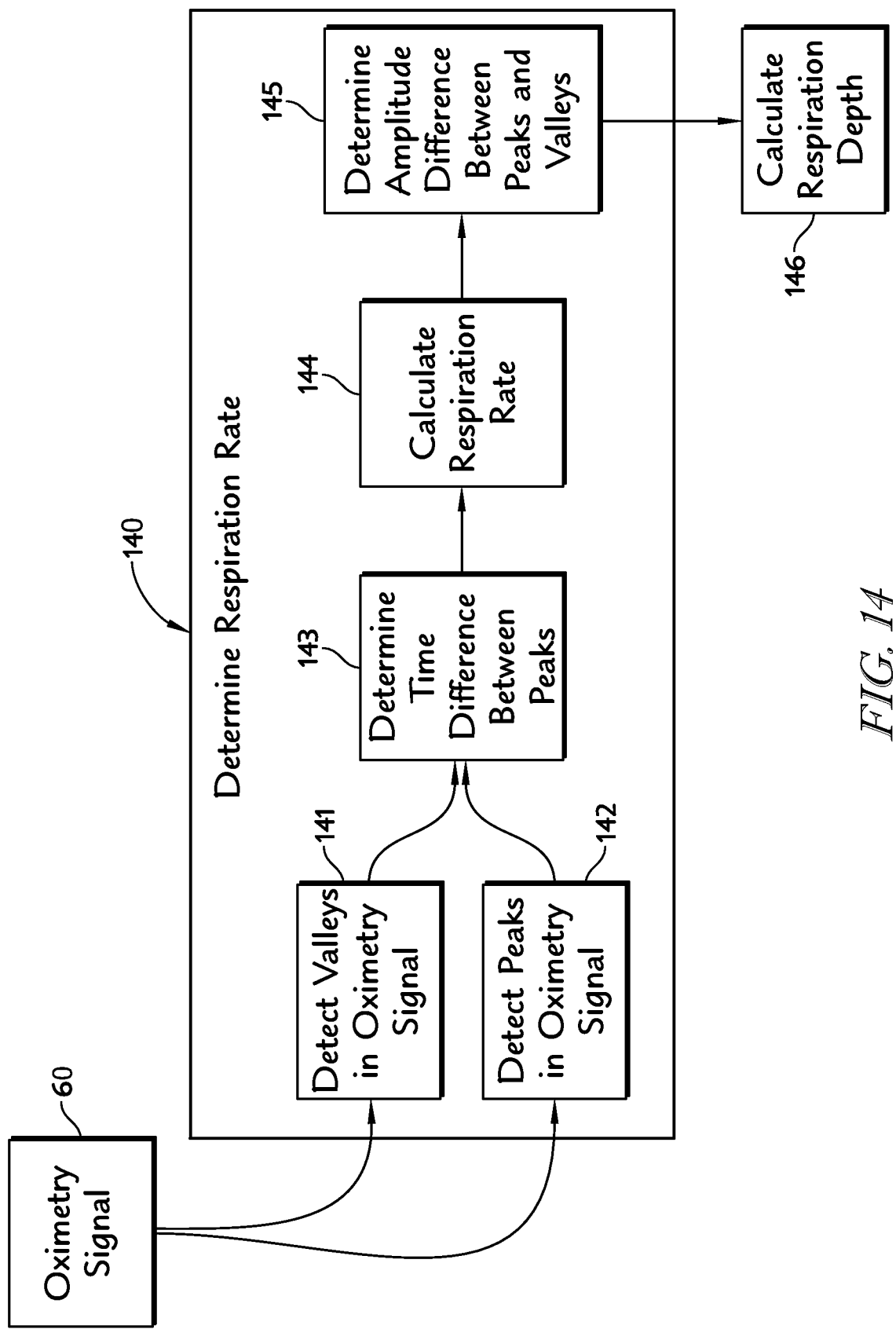
Figure 15:
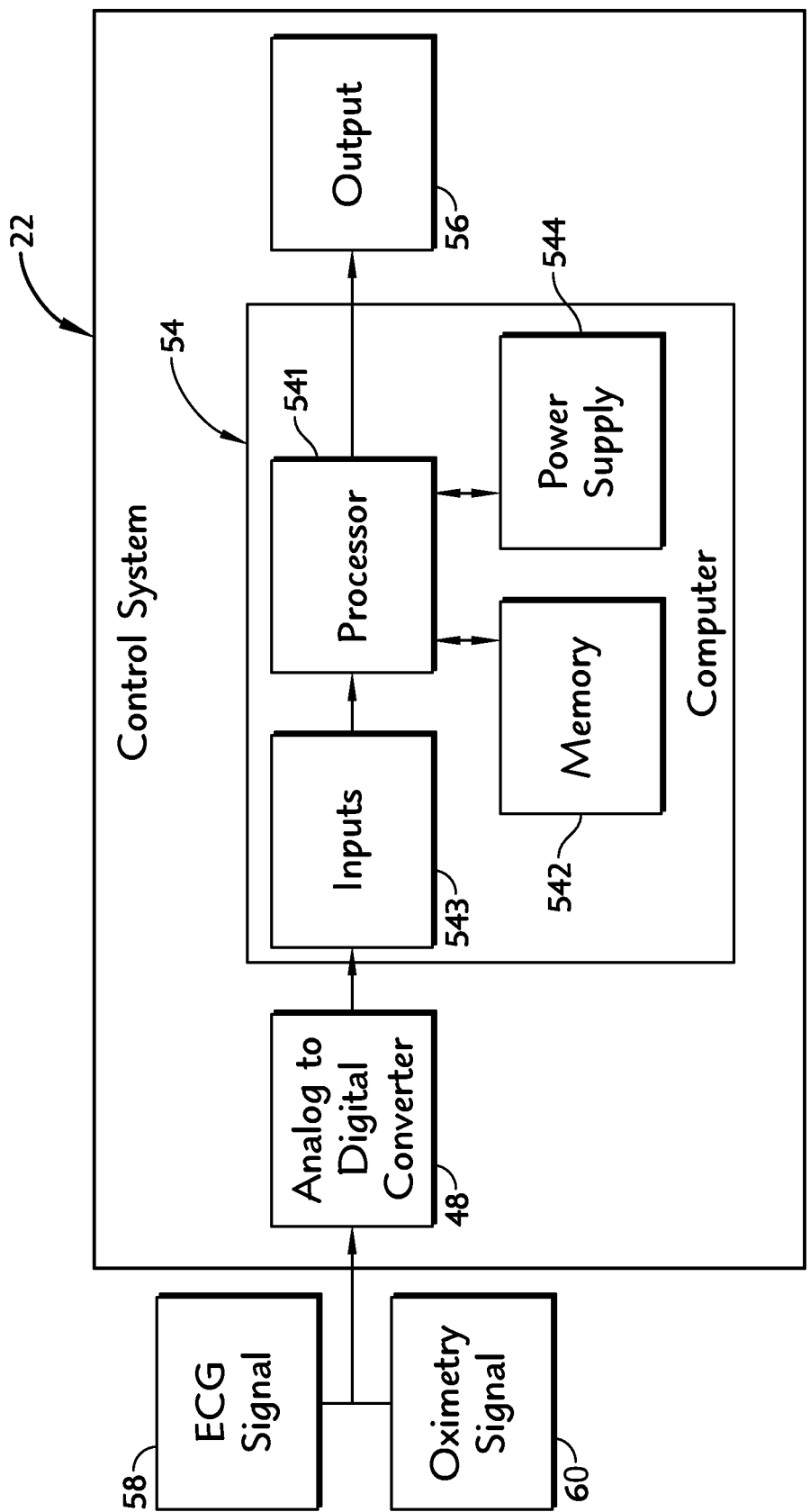
Figure 16:
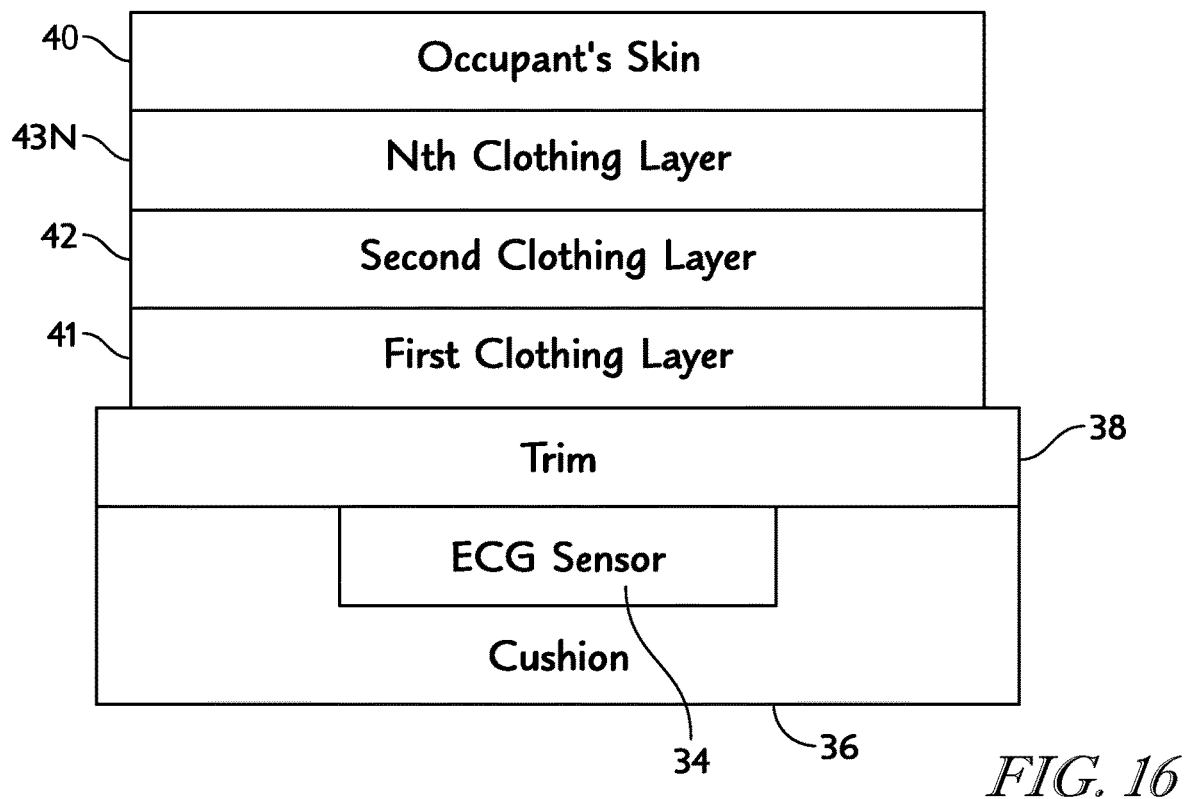
Figure 17:
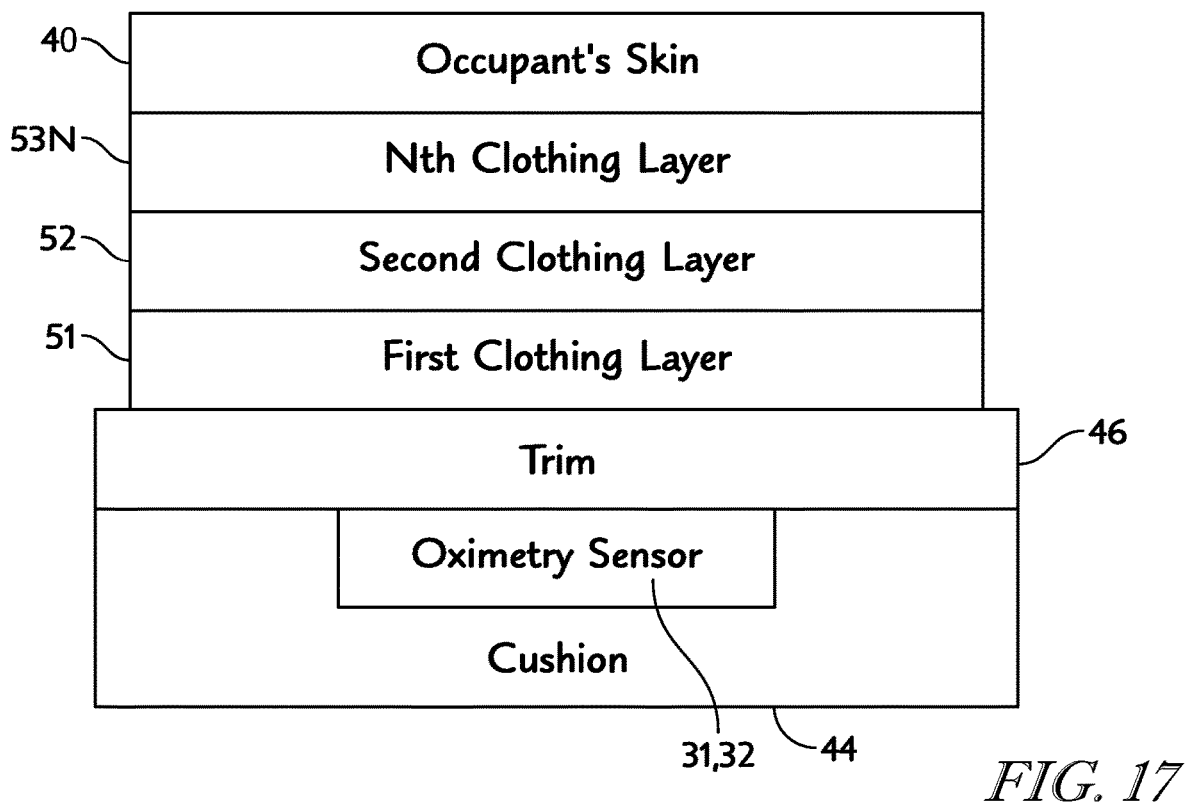
Figure 18:
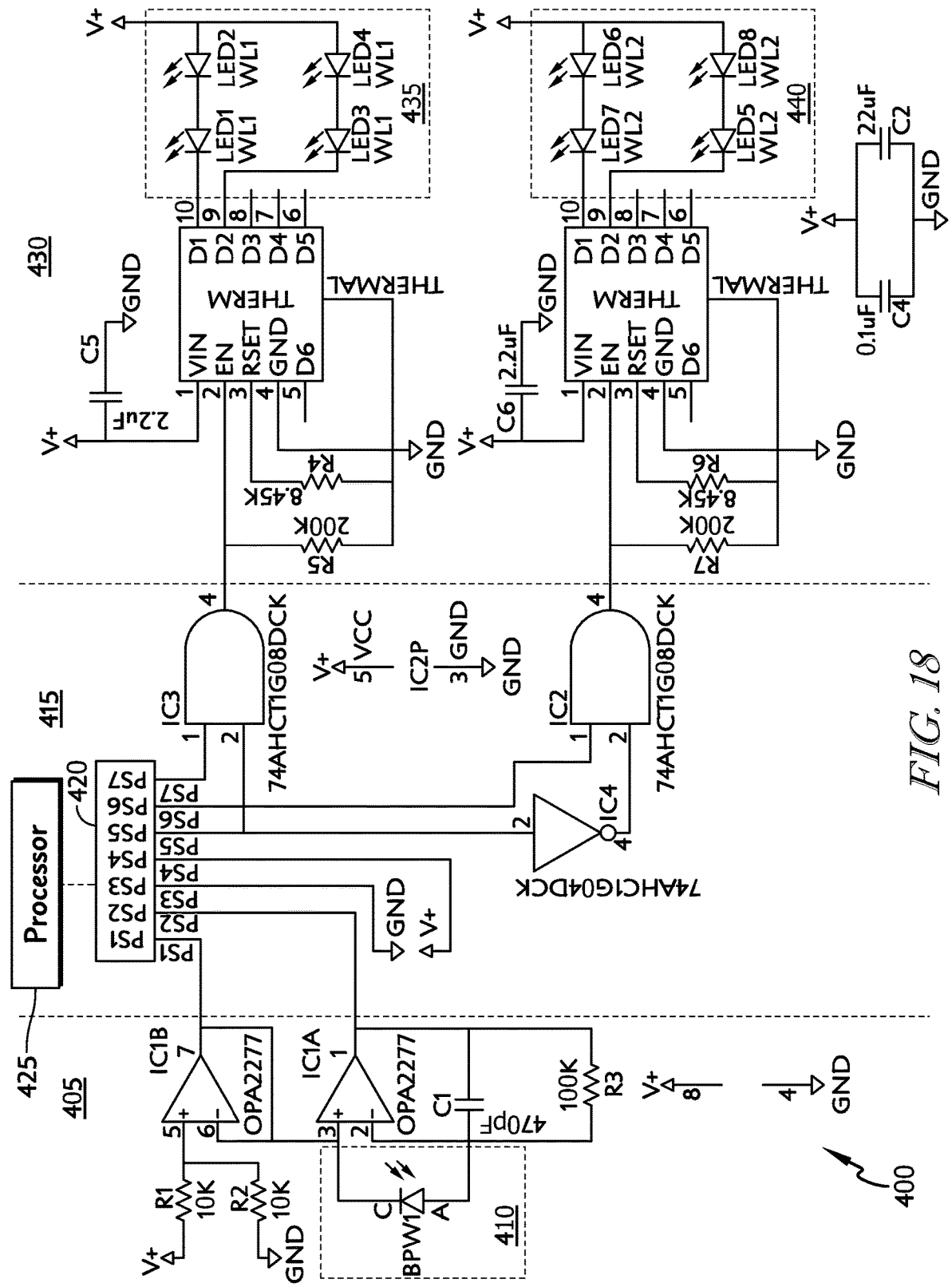

FIG. 8 is a diagrammatic view of an electronics system included in the vehicle seat of FIG. 1 showing that the electronics system includes an ECG sensor system including a first ECG receiver, a second ECG receiver, an ECG unit, and a ECG mat, an oximetry sensor system including a first oximetry sensor and a second oximetry sensor, and a control system including an analog to digital converter, a computer, and an output;

FIG. 9 is a diagrammatic view of an ECG signal-acquisition process showing that the ECG signal is acquired by obtaining electrical signals from the occupant, transforming the electrical signals through a driven right leg circuit, passing the transformed signals through the ECG-sensor mat to remove noise, passing the signals through the occupant to remove noise, converting the signal from analog to digital, and filtering the signal to remove noise and suggesting that the ECG signal may be used to determine heart rate, heart-rate variability, and stress level and combined with the oximetry signal to determine pulse-transit time and blood pressure;

FIG. 10 is a diagrammatic view of an oximetry signal-acquisition process showing that the oximetry signal is acquired by obtaining oximetry signals, converting the oximetry signals from analog to digital, filtering the signals to remove noise, and determining the best oximetry signal from the two available signals and suggesting that the oximetry signal may be used to determine respiration, respiration rate, and respiration depth and that the oximetry signal may be combined with the ECG signal to determine pulse-transit time and blood pressure;

FIG. 11 is a diagrammatic view of a heart-rate determination process including the steps of detecting heart beats from the ECG signal, differentiating the signal, determining a raw heart rate, determining reliability of each signal, weighing more reliable signals, and calculating an average heart rate;

FIG. 12 is a diagrammatic view of a heart rate variability determination process including the steps of taking the derivative of the average heart rate, determine the Heart Rate Variability (HRV) spectrum, determining a ratio of high frequencies to low frequencies, and determining the impact of adrenaline and other neurotransmitters on heart rate and suggesting that understanding which neurotransmitters are affecting heart rate may be used to determine a stress level of the occupant;

FIG. 13 is a diagrammatic view of a pulse-transit time acquisition process and a blood-pressure acquisition process showing that the pulse-transit time acquisition process includes the steps of detecting peaks in the ECG signal, detecting peaks in the oximetry signal, determining time between peaks in the oximetry signal, and calculating pulse-transit time and showing that the blood-pressure acquisition process includes the steps of transforming the pulse-transit time signal and estimating systolic blood pressure and diastolic blood pressure;

FIG. 14 is a diagrammatic view of a respiration-rate determination process including the steps of detecting peaks in the oximetry signal, detecting valleys in the oximetry signal, determining time difference between peaks, calculating a respiration rate, and determining a difference in amplitude between the peaks and valleys to calculate a respiration depth;

FIG. 15 is a diagrammatic view of the control system of FIG. 8 showing that the computer includes inputs coupled to the analog to digital converter to receive the ECG and oximetry signals, a processor configured to execute instructions stored in memory, and a power supply coupled to the processor to provide power;

FIG. 16 is a diagrammatic view of another embodiment of a seat back in accordance with the present disclosure showing that the seat back includes a seat cushion and trim surrounding the seat cushion and that an ECG sensor may be coupled to the seat cushion to lie below the trim to sense an occupant's electrical signals through the trim and multiple layers of clothing;

FIG. 17 is a diagrammatic view of another embodiment of a seat bottom in accordance with the present disclosure showing that the seat bottom includes a seat cushion and trim surrounding the seat cushion and that the oximetry sensor may be coupled to the seat cushion to lie below the trim to sense oxygen content of the occupant's blood through the trim and multiple layers of clothing;

FIG. 18. is an exemplary schematic diagram showing electronic components included in an oximetry sensor assembly provided in accordance with the present disclosure; and FIG. 19 provides a table that includes additional information regarding the electronic components shown in FIG. 18.

DETAILED DESCRIPTION

It should be understood that the appended drawings are not necessarily to scale, presenting a somewhat simplified representation of various features illustrative of the basic principles of the present disclosure. The specific design features of the present disclosure as disclosed herein, including, for example, specific dimensions, orientations, locations, and shapes will be determined in part by the particular intended application and use environment.

In the figures, reference numbers refer to the same or equivalent parts of the present disclosure throughout the several figures of the drawings. Thus, unless otherwise stated, such elements have similar or identical structural, dimensional, and material properties.

A vehicle seat 10, in accordance with the present disclosure, includes a seat bottom 12, a seat back 14, and an electronics system 16 as shown FIG. 1 and suggested in FIG. 8. Seat back 14 is preferably coupled to seat bottom 12 to extend in an upward direction away from seat bottom 12. Electronics system 16 is configured to sense one or more physiological attributes of an occupant (not shown) sitting on vehicle seat 10 through clothing worn by the occupant, so that a predetermined action may be taken in response to the physiological attribute detected by electronics system 16. In one illustrative example, the predetermined action may be audio, visual, or tactile feedback provided by vehicle seat 10 to the occupant.

As shown in FIG. 8, electronics system 16 comprises an electrocardiogram (ECG) sensor system 18, an oximetry sensor system 20, and a control system 22. ECG sensor system 18 is preferably coupled to seat back 14 and seat bottom 12 to sense electrical signals provided by the occupant. Oximetry sensor system 20 is preferably coupled to seat bottom 12 to sense oxygen content in the occupant's blood. Control system 22 is coupled to the ECG sensor system 18 and oximetry sensor system 20 to receive signals provided by each system, process the signals, make calculations using the signals, and determine physiological attributes of the occupant. Control system 22 may perform one or more predetermined actions based on the physiological attributes of the occupant.

ECG sensor system 18 of FIG. 8 includes, for example, a first ECG receiver 24, a second ECG receiver 26, an ECG mat 28, and an ECG unit 30 as suggested in FIGS. 1, 2, 4, 5, and 8. First and second ECG receivers 24, 26 are coupled to seat back 14 to lie in spaced-apart relation to one another and lie in spaced-apart relation above seat bottom 12. ECG mat 28 is coupled to seat bottom 12 and preferably arranged to lie under the thighs of an occupant 50. In one example, ECG receivers 24, 26 are aligned with an occupant's chest and arranged to sense electrical signals provided by the occupant's body. The sensed electrical signals are then transformed by a driven right leg circuit included in ECG unit 30, and passed through ECG mat 28 located in seat bottom 12 as suggested in FIG. 8. ECG mat 28 then sends the signals back through occupant 50 where the signals are detected again by ECG receivers 24, 26, passed through ECG unit 30 and sent to control system 22. As a result, ECG sensor system 18 minimizes noise so that the remaining signal is associated more closely with an occupant's heart rate.

Figure 2:
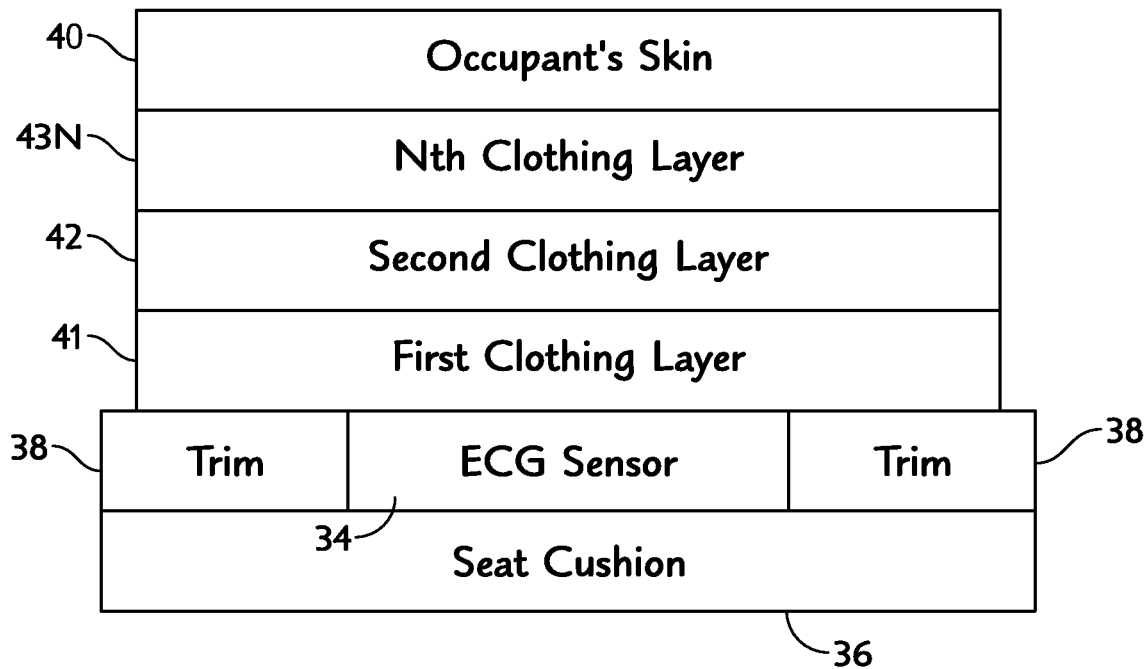

First and second ECG receivers 24, 26 and ECG mat 28 cooperate to provide an ECG sensor 34. ECG sensor 34 is coupled to a seat cushion 36 and surrounded by trim 38 as shown in FIG. 2. ECG sensor 34 is configured to provide means for detecting electrical signals in occupant 50 through first, second, and $N^{th}$ clothing layers 41, 42, and 43N as shown in FIG. 2. In one example, first clothing layer 41 is a shirt made of cotton. Second clothing layer 42 is an undershirt made from cotton. Nth clothing layer 43N may be yet another undershirt made from polyester. $N^{th}$ clothing layer 43N may be one layer or may be additional layers.

Figure 3:
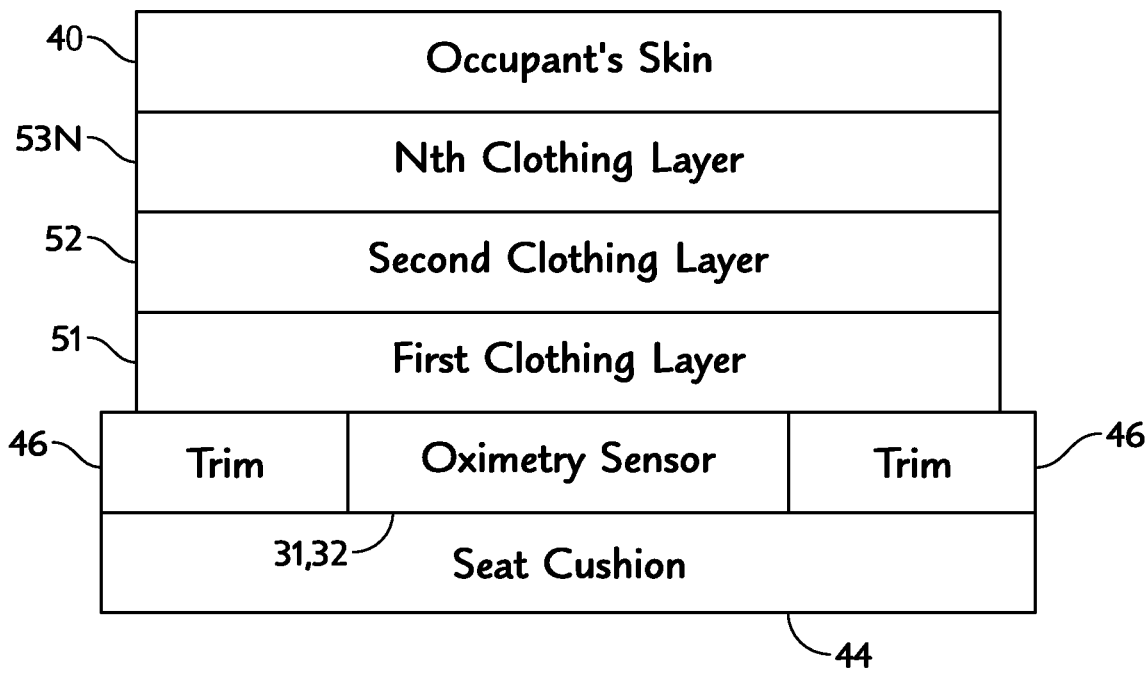
Figure 4:
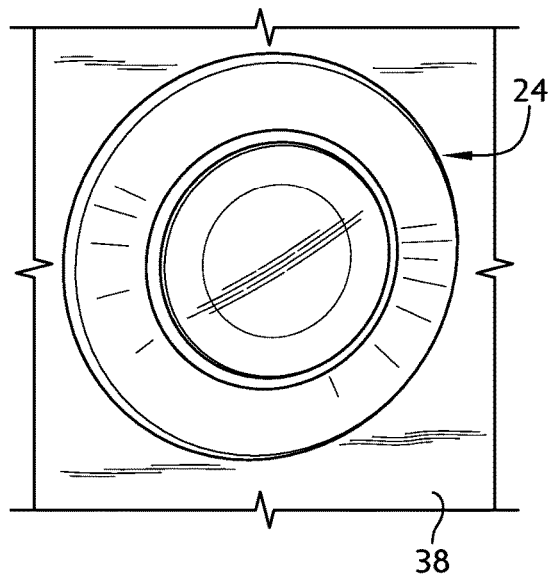
FIG. 4 is an enlarged partial perspective view of the ECG sensor of FIG. 1.
Figure 5:
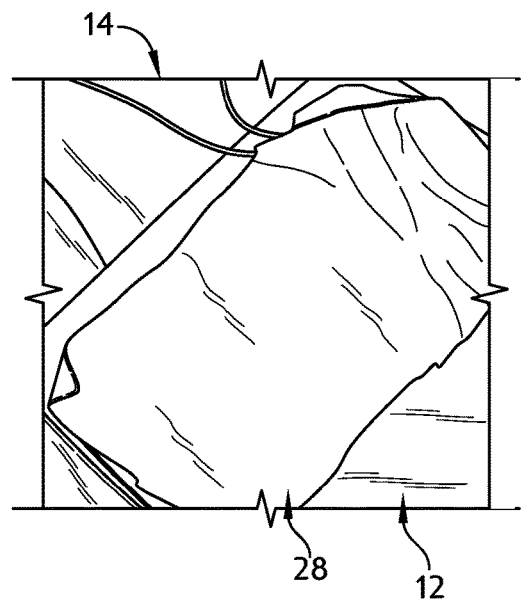
FIG. 5 is an enlarged partial perspective view of the sensor mat of FIG. 1 with the trim removed from the seat bottom to reveal the sensor mat.
Figure 6:
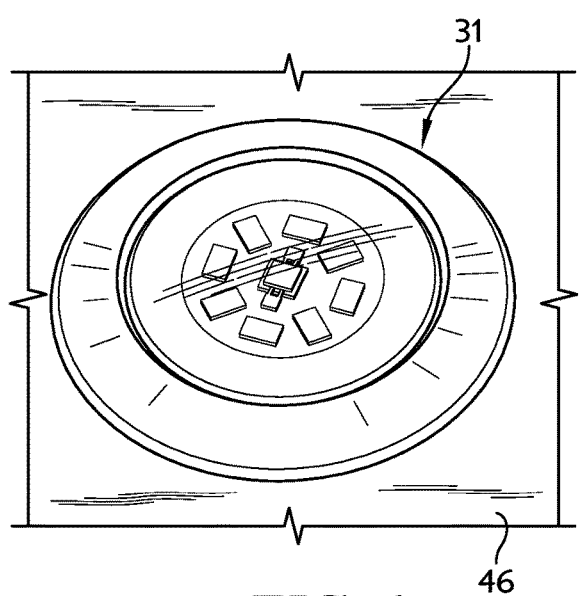
FIG. 6 is an enlarged partial perspective view of the oximetry sensor of FIG. 1 showing that the oximetry sensor includes eight LED emitters positioned to lie around a central light receiver.
Figure 7:
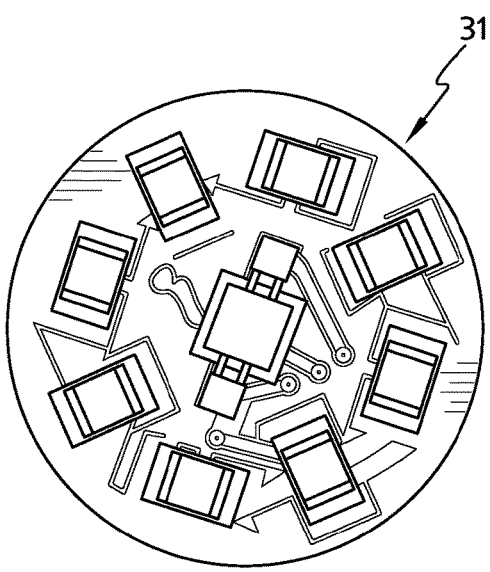
FIG. 7 is a photograph of the oximetry sensor of FIG. 1 separated from a sensor mount and a sensor shield removed to expose underlying circuitry included in the oximetry sensor.

Oximetry sensor system 20 includes a first oximetry sensor 31 and a second oximetry sensor 32 as shown in FIGS. 1 and 8. Oximetry sensors 31, 32 are preferably coupled to seat bottom 12 as shown in FIGS. 1, 3, and 6. Oximetry sensors 31, 32 are spaced apart from one another and spaced apart from ECG mat 28 as shown in FIG. 1. Each oximetry sensor 31, 32 is arranged to underlie an associated leg of the occupant and is arranged to sense oxygen content in the occupant's blood. Each oximetry sensor 31, 32 emits light at a wavelength which passes through clothing layers 41, 42, 43N and enters occupant's skin 40 where a portion of the light is absorbed by the occupant's blood. The remaining portion of the light is reflected by the occupant's blood back through clothing layers 41, 42, 43N and is detected by each oximetry sensor 31, 32. The detected light is converted to an oximetry signal and sent to control system 22.

With regard to oximetry sensors 31, 32, and for purposes of background, oxygen saturation refers to oxygenation, or when oxygen molecules ($O_2$) enter the tissues of the human body. In the human body, blood is oxygenated in the lungs, where oxygen molecules travel from the air and into the blood. Oxygen saturation, also called $O_2$ sats, is a measure of the percentage of hemoglobin binding sites in the bloodstream occupied by oxygen. Measurement of a subject's oxygen saturation provides one indication of the subject's overall health and, more particularly, the subject's pulmonary and cardiovascular health as both the pulmonary and cardio-vascular systems cooperate with each other and other systems of the human body to perform oxygenation. Arterial oxygenation is measured typically using pulse oximetry, which is a non-invasive technology for monitoring the saturation of a subject's hemoglobin.

In transmissive pulse oximetry techniques, a sensor is placed on a thin part of a subject's body, for example, a fingertip or earlobe, or in the case of an infant, across a foot. Light of two different wavelengths is passed through the subject's tissue to a photodetector. The changing absorbance at each of the wavelengths is measured, allowing determination of the absorbances due to the pulsing arterial blood alone, excluding venous blood, skin, bone, muscle, and fat. Another type of pulse oximetry is reflectance pulse oximetry. Reflectance pulse oximetry may be used as an alternative to transmissive pulse oximetry described above. Reflectance pulse oximetry does not require a thin section of a subject's body. Therefore, reflectance pulse oximetry is better suited to more universal application such as measurement of blood oxygen concentration in the feet, forehead, and chest. However, reflectance pulse oximetry also has some limitations.

Pulse oximetry is based on the principal that oxy- and deoxy-hemoglobin have different light absorption spectra. Reflective pulse oximetry measures the light absorption of light of two different wavelengths via reflectivity; that is, by knowing the amount of light transmitted and detecting the amount of light reflected using a photodector or similar sensor, one is able to determine the amount of light absorbed by the subject's body, i.e., the light absorption. However, the efficacy of non-contact pulse oximetry through intervening materials is subject to the absorption spectra of those materials.

In one embodiment, oximetry sensors 31, 32 are oximetry sensors, also called PulseOx sensors, which are configured to determine blood oxygenation through a variable makeup of intervening materials, and are configured with the ability to switch between or select from multiple wavelengths of light to be transmitted at the subject's body. Based on the reflected amount of light resulting from the various wavelengths, the sensor assembly is able to select one or more optimum wavelengths of light to be transmitted at the subject's body to determine the oxygen saturation for the subject via reflective pulse oximetry. One exemplary oximetry sensor is disclosed in U.S. Provisional Patent Application Ser. No. 61/730,374 filed Nov. 27, 2012, the contents of which is incorporated by reference in its entirety herein.

FIG. 18 is a schematic diagram illustrating electronic components of a sensor assembly provided in accordance with disclosed embodiments. As shown in FIG. 18, at least one disclosed embodiment of the sensor assembly 400 includes three exemplary stages: a photodetector stage 405, an input/output and processing stage 415 and a light emission stage 430. Photodetector stage 405 includes a photodetector or photodiode 410 that is used to detect reflected amounts of light from a subject's body. Photodetector stage 405 also includes various circuitry elements that enable buffering and filtering of the detected signal including operational amplifiers for establishing a virtual ground and buffering and filtering of the signal output from the photodetector 410.

The teachings of U.S. Pat. No. 5,348,004, entitled "Electronic Processor for Pulse Oximeter" and U.S. Pat. No. 6,839,580, entitled "Adaptive Calibration for Pulse Oximetry" are both hereby incorporated by reference herein in their entirety. Each of those patents disclose various equipment, components, and methodology that may be used to implement the disclosed embodiments for sensing and monitoring blood oxygen in a seating environment.

The output of photodetector stage 405 is coupled to the input/output and processing stage 415 so as to enable analysis of the signal detected by the photodetector to perform calibration of the sensor assembly and detection and monitoring of the subject's blood oxygen content. The input/output and processing stage 415 includes a communication bus 420 that couples the sensor assembly components of stages 405 and 430 with the processor 425. This coupling and associated bidirectional communication enables the processor 425 to control emission of light via the light emission stage 430 and receive reflected signals from the photodetector stage 405 to perform processing for calibration, detection, and monitoring of the subject's blood oxygen content.

Light emission stage 430 includes one or two banks of LEDs 435, 440. The LED banks may be optimized to use off-the-shelf LEDs at, for example, 850 nm and 950 nm light that penetrate a wide range of materials well. The light emission stage 430 may use additional or alternative banks of LEDs, for example, at additional wavelengths between 600 nm and 1100 nm for greater robustness of signal to noise determination. In implementation, the stages illustrated in FIG. 18 and the incorporated components are selected from commercially available electronics components listed in the table of FIG. 19. Further, it should be noted that the photodiode 410, i.e. the receptor, and the LEDs of the LED banks 435, 440, i.e., the emitter, may be approximately 7.5 mm to avoid spill over from the LEDs to the photodiode.

Embodiments disclosed herein provide the ability to perform noninvasive, non-distracting monitoring of blood oxygen contact through multiple layers of material. A calibration sub-routine for sensor and sensor assembly learns the best light components for a particular subject being monitored. This is because the light components used for reflective monitoring change depending on the amount, type, and number of clothing layers for a particular subject. Thus, disclosed embodiments may use custom designed circuitry developed to read PulseOx (also known as photoplesythmography, or PPG) signals through variable layers of intervening clothing worn by a subject. Thus, disclosed embodiments enable sensor assembly calibration cycling through multiple wavelengths of light to enable a spectral analysis of materials and oxy/deoxy-hemoglobin absorption to ascertain optimal wavelengths for material penetration and determination of oxygen saturation curves while maximally identifying movement and other artifacts.

Disclosed embodiments of the sensor assembly may also be configured to perform auto-calibration, which enables the ability to penetrate an unknown makeup of intervening material to read changes in reflected light that accompany fluctuations in oxy- and deoxy-hemoglobin accompanying each heartbeat. Because some of the relevant aspects of PulseOx signals change at very slow time-scales (e.g., respiration changes 10+ seconds), simply using high-pass filtering of the signal merely creates substantial distortions and delays. To avoid the problems of high-pass filters, custom circuitry and algorithms were developed, and are disclosed in U.S. Provisional Patent Application Ser. No. 61/730,374, referenced above.

Referring back to FIG. 8, control system 22 is configured to communicate with each oximetry sensor 31, 32 to command each oximetry sensor 31, 32 to execute an auto-calibration process each time an occupant sits on vehicle seat 10. The auto-calibration process causes the amount of light emitted from oximetry sensors 31, 32 to be varied. In on example, high-frequency pulse width modulation is used to vary the light being emitted. However, a digitally controlled potentiometer may also be used. Light levels are increased in a stepped manner until sufficient light is reflected back from occupant's skin through multiple layers of clothing. Each time an occupant sits on vehicle seat 10, the number of layers and type of layer may change. As a result, the amount of light required to pass through the clothing layers, be reflected from the occupant's skin, and pass back through the clothing layers to provide an indication of oxygen content in the occupant's blood also may change. The auto-calibration process causes the light output to gradually increase until a sufficiently strong signal is returned without causing the oxygen content to be drowned out by excess light.

Oximetry sensors 31, 32 are coupled to a seat cushion 44 included in seat bottom 12 and surrounded by trim 46 as shown in FIG. 3. Oximetry sensors 31, 32 are configured to detect oxygen content in an occupant's blood through first, second, and Nth clothing layers 51, 52, and 53N as shown in FIG. 3. In one example, first clothing layer 51 is a pair of pants made from denim. Second clothing layer 52 is a pair of underpants made from cotton. Nth clothing layer 53N may be a pocket included in the pair of pants or any other suitable alternative. Nth clothing layer 53N may be one layer or multiple layers.

Control system 22 includes an analog to digital converter 48, a computer 54, and an output 56 as shown in FIG. 8. Once the oximetry signals and the ECG signal are obtained, the analog signals are then converted to digital signals by analog to digital converter 48. The digital signals are then processed by computer 54. The signals may be processed by computer 54 to determine a heart rate 61, blood pressure 62, respiration rate 63, and stress level 64 as shown in FIG. 1. Processes for determining heart rate 61, blood pressure 62, respiration rate 63, and stress level 64 are shown in FIGS. 9-14.

An ECG-signal acquisition process 70 is shown, for example, in FIG. 9. ECG-signal acquisition process 70 includes the steps of obtaining 71 electrical signals from occupant 50, transforming 72 the electrical signals in ECG unit 30, passing 73 signals through ECG mat 28, passing 74 the signal through occupant 50, coverting 75 the analog signal to a digital signal, and filtering 76 the signal to provide an ECG signal for use by computer 54. Computer 54 uses the ECG signal to determine heart rate 61, heart-rate variability 65, stress level 64, a pulse-transit time 66, and blood pressure 62 as shown in FIG. 9. ECG signal 58 is obtained when first and second ECG receivers 24, 26 sense electrical signals in occupant 50. Based on the output of the processing, computer 54 may perform a predetermined action. The predetermined action may be storing the calculated values in memory 542 of computer 54. The predetermined action may be activating output 56 to communicate the output to the occupant.

Obtaining step 71 obtains electrical signals from occupant 50 as shown in FIG. 8. ECG receivers 24, 26 sense electrical signals from occupant 50. Those sensed electrical signals are then passed (1) to ECG unit 30 which are then passed (2) through ECG mat 28 which communicates (3) the signals back to occupant 50. First and second ECG receivers 24, 26 then sense (4) the signal a second time which has been cleaned and amplified. The signal is once again communicated (1) to ECG unit 30 which then communicates (5) the signal to analog to digital converter 48 as shown in FIG. 8.

An oximetry signal acquisition process 80 is shown, for example, in FIG. 10. Oximetry signal acquisition process 80 includes the steps of obtaining 81 oximetry signals from occupant 50, converting 82 the analog signals to digital signals, filtering 83 the digital signals to remove noise, and determining 84 the best oximetry signal from the two oximetry sensors 31, 32. Computer 54 uses the oximetry signal to calculate pulse-transit time 66, blood pressure 62, respiration 67, a respiration rate 68, and respiration depth 69 as shown in FIG. 10. Oximetry signal 60 is obtained when first and second oximetry sensors 31, 32 sense oxygen content in occupant's blood. Based on the output of the processing, computer 54 may activate output 56.

Obtaining step 81 obtains oximetry signals from occupant 50 as shown in FIG. 8. In a first sub-step, each oximetry sensor 31, 32 emits (1) light which passes through the occupant's clothing and passes into occupant 50. A portion of the light is then reflected (2) back from occupant 50 and captured by each associated oximetry sensor 31, 32. Each oximetry sensor 31, 32 then takes the captured light and coverts (3) it to a signal which is then communicated to analog to digital converter 48 as shown in FIG. 8.

Heart rate 61 is calculated by computer 54 using heart-rate determination process 90 as shown in FIG. 11. Heart-rate determination process 90 includes the steps of detecting 91 heart beats from the ECG signal, differentiating 92 the heart-beat signal, determining 93 a raw heart rate, determining 94 reliability of each signal, weighing 95 more reliable signals, and calculating 96 an average heart rate (FIG. 10, ref. 61). Detecting step 91 detects heart beats preferably uses threshold and peak detection of ECG signal 58. Determining step 94 determines the reliability of each signal. In one example, determining step 94 uses peak analysis to remove erroneous data, the root mean square of the signal to determine stronger signals, and signal to noise ratio to determine more reliable signals. Once heart rate data is determined from 90, further determinations may be made regarding heart-rate variability 100 and stress level 110, discussed below.

Once heart rate 61 is determined by computer 54 in heart-rate determination process 90, computer 54 may then proceed to a heart-rate variability determination process 100 as shown in FIG. 12. Heart-rate variability determination process 100 includes taking 101 a derivative of the heart rate, determining 102 heart rate variability spectrum by taking a Fourier transform of the signal, determining 103 a ratio of high frequencies to all frequencies, and determining 104 the impact of adrenaline on the occupant. Adrenaline affects the lower frequencies of heart rate variability. As a result, if the lower frequencies are driving heart rate variability, computer 54 may proceed to stress-determination step 110 as shown in FIG. 12. In stress-determination step 110, computer 54 identifies that the occupant is under stress when adrenaline is increasing.

Determining step 103 includes calculating a ratio of high frequencies to all frequencies. As an example, LF is the power contained in low frequencies (0.05-0.125 Hz) and HF is the power contained in high frequencies (0.2-0.3 Hz).

$$\text{LH2HF ratio} = \frac{\text{LF}}{(\text{LF} + \text{HF})}$$

$$\text{Emotional Stress} = \sqrt{\frac{\text{LF}}{(\text{LF} + \text{HF})}}$$

In this example, as the value approaches zero percent, an occupant's stress level is the lowest. As the value approaches 100 percent, the occupant's stress level is the highest.

Computer (54) may combine ECG signal 58 and oximetry signal 60 to obtain pulse-transit time 66 and blood pressure 62 as shown in FIG. 13. Computer (54) performs a pulse-transit time determination process 120. Pulse-transit time determination process 120 includes the steps of detecting 121 peaks in ECG signal 58, detecting 122 peaks in oximetry signal 60, determining 123 time between peaks in oximetry signal 60, and calculating 124 pulse-transit time 66. Once pulse-transit time 66 is determined by computer 54, computer 54 proceeds to a blood-pressure determination process 130 as shown in FIG. 13. Blood-pressure determination process 130 includes the steps of transforming 131 pulse-transit time 66, estimating 132 systolic blood pressure, and estimating 133 diastolic blood pressure as shown in FIG. 13.

Blood-pressure determination process 130 may be further improved by adding an occupant's anthropomorphic data into the calculation. Specifically, knowledge about a distance between an occupant's heart and the location on the occupant's leg where one of the oximetry sensors is taking a measurement could improve accuracy. Faurecia's SMARTFIT® technology may be used to provide such anthropomorphic data to computer 54.

Computer 54 may use only oximetry signal 60 to determine respiration rate 68 and respiration depth 69 as shown, for example, in FIG. 14. Computer 54 performs a respiration-rate determination process 140 that includes the steps of detecting 141 valleys in oximetry signal 60, detecting 142 peaks in oximetry signal 60, determining 143 time between the peaks, calculating 144 respiration rate 68, and determining 145 amplitude difference between peaks and valleys as shown in FIG. 14. Once the amplitude difference is determined, computer 54 may proceed to calculating 146 respiration depth 69. Respiration rate 68 and respiration depth 69 may be useful in determine an emotional state of occupant 50, awareness of occupant 50, alertness of occupant 50, and other suitable health and/or physiological indicators.

Computer 54 executes the various processes described above using a processor 541 included in computer 54 as shown in FIG. 15. The processes 70, 80, 90, 100, 110, 120, 130, and 140 are stored, for example, in memory 542 of computer 54 which is coupled to processor 541. Computer 54 further includes inputs 543 and power supply 544. Inputs 543 are arranged to interconnect processor 541 and analog to digital converter 48 so that ECG signal 58 and oximetry signal 60 may be communicated to processor 541 for processing. Processor 541 is further coupled to output 56 as shown in FIGS. 8 and 15. Power supply 544 is coupled to processor 541 and configured to provide power to processor 541 and memory 542.

In one example, computer 54 is located in vehicle seat 10 and coupled to a controller area network included in the vehicle. In another example, computer 54 is located in spaced-apart relation to vehicle seat 10 and may be a computer which controls other equipment in the vehicle. In either example, output 56 may be used to provide audio, visual, or tactile feedback.

In one example, output 56 may be a video screen located in the vehicle which provides output from computer 54 and receives input from the occupant. Such input may be captured through one of inputs 543 and communicated to processor 541 for further processing. In another example, output 56 may also be an instrument panel included in the vehicle. In another example, output 56 may be a personal computer, a mobile device or smart phone, or communication device which sends data provided by processors 541 remotely. Data may be sent remotely to a doctor, a vehicle manufacturer, or any other suitable alternative. In the example of a doctor, the data may be used to prescribe treatments which may be performed with or without the vehicle seat. In another example, output 56 may be an actuator included in vehicle seat 10 which moves portions of vehicle seat 10. In this example, the actuator may be use to adjust an angle at which seat back 14 extends upwardly away from seat bottom 12.

Electronics system 16 obtains sensor data from signals obtained and computer 54 processes the signals to obtain information related to occupant 50. Electronics system 16 may cooperate with seat bottom 12, seat back 14, other vehicle systems, and systems separate from the vehicle to maximize occupant comfort, maximize occupant capacity to control the vehicle, maximize occupant health, and maximize the emotional well being of the occupant.

Occupant comfort may be maximized according to several exemplary modes such as an auto-fit mode, a smart-memory mode, a pro-active comfort mode, a pro-active thermal-adjustment mode, a next-position mode, a comfort-validator mode, a smart-massage mode, a targeted heating and cooling treatment mode, a recommended break-activity mode, a better circulation mode, a tension relief mode, an energize mode, and an arrival coach mode.

An auto-fit mode may use sensor data collected by electronics system 16 and other data communicated to computer 54 via input 543 to change the position and orientation of vehicle seat 10 and other components in the vehicle automatically. As a result, the occupant's comfort is maximized according their physiological data.

A smart-memory mode may use sensor data collected by electronics system 16 to determine an identity of the occupant and save settings of vehicle seat 10 according to the identity of the occupant. As a result, the electronics system 16 may position vehicle seat 10 and vehicle equipment according to the stored profile of the occupant associated with the identified identity.

A pro-active comfort mode may use sensor data collected by electronics system 16 to predict physical or thermal discomfort and make changes in response. Changes may occur before the occupant recognizes physical or thermal discomfort. The sensor data may be processed by computer 54 and compared with known or learned trends to predict physical or thermal discomfort. Computer 54 may learn that when certain sensor data occurs, an occupant manually performs an action such as turn down a blower included in the vehicle's HVAC system.

The pro-active thermal-adjustment mode may use sensor data collected by electronics system 16 to predict thermal discomfort and make changes in response. In one example, electronics system 16 may sense of thermal discomfort on an occupant's face and command via output 56 the vehicle's Heating, Ventilation, and Air Conditioning (HVAC) system to provide reduced heating or cooling only to the occupant's face.

A next-position mode may use sensor data collected by electronics system 16 to calculate a new arrangement of the vehicle seat based on known physiological data such as the dimensions of an occupant's body parts. As a result, computer 54 through output 56 commands vehicle seat 10 to make adjustments in position and orientation to further maximize patient comfort according to real-time sensor data.

A comfort-validator mode may use sensor data collected by electronics system 16 to determine if changes made by computer 54 via output 56 have resulted in objective measures of improved comfort. As a result, an occupant may determine if their comfort has actually improved as compared to whether they think it has improved.

A smart-massage mode may use sensor data collected by electronics system 16 and output 56 to provide constantly improving treatments to a specific occupant's stress and fatigue. In one example, a first massage algorithm may be established to treat an occupant. During the trip, the electronics system 16 may determine that a second different massage algorithm should be established to further mitigate the occupant's stress and fatigue.

A targeted heating and cooling treatment mode may use sensor data collected by electronics system 16 and output 56 to command the vehicle's Heating, Ventilation, and Air Conditioning (HVAC) system to provide localized heating or cooling to the occupant. As a result, energy used to provide thermal comfort to the occupant is minimized while occupant comfort is maximized.

A recommended break-activity mode may use sensor data collected by electronics system 16 before a break from travel is taken by the occupant and after a break is taken from travel by the occupant to determine the most effective break activities for use by the occupant. As an example, computer 54 may learn over time that when the occupant drives for at least two hours, the most effective break activity for the occupant is a specific stretching routing by comparing sensor data obtained before and after other break activities. In addition, computer 54 may determine that the previously performed break activities were insufficient and prescribe new break activities by monitoring post-break sensor data.

A better circulation mode may use sensor data collected by the electronics system 16 to determine that blood flow in one or more locations of an occupant is or may soon be poor. In one example, the oximetry sensors in the seat may be used by computer 54 to determine trends relating to blood flow. As a result, computer 54 may command through outputs 56 various features of the vehicle and vehicle seat to engage and maximize circulation in the occupant. In one example, computer 54 may command massage to be provided by the vehicle seat. In another example, computer 54 may command the vehicle seat to actuate changing and orientation of the vehicle seat to promote increased circulation. In yet another example, computer 54 may command heat to be applied to the occupant by the vehicle seat. In yet another example, computer 54 may suggest that a break be taken by the occupant and one or more break activities (e.g., stretching, walking, etc.) by the occupant.

A tension relief mode may use sensor data collected by the electronics system 16 to determine a tension level of an occupant. In one example, tension may be characterized as a measure of muscle tension of the occupant. Muscle tension may be determined from inputs such as stress, posture, and pressure exerted on the occupant. In one illustrative scenario, computer 54 may determine that an occupant is experiencing high tension. As a result, computer 54 may ask the occupant if the occupant wants to decrease sensed tension through use of one or more features. In another example, computer 54 may detect increased tension and automatically engage one or more features to minimize the occupant's tension.

In one example, computer 54, via output 56, may command massage to be provided by the vehicle seat. Various characteristics of massage may be varied by computer 54 to minimize tension such as frequency, intensity, location, and patterns of application to the occupant.

In another example, computer 54 may command application of heat or cooling to the occupant using the vehicle seat and or the vehicle heating and cooling systems to minimize tension. Various characteristics of heating and cooling include location of application, temperatures applied, duration, and patterns of application to the occupant. Patterns of application may include alternating hot and cold or slowly increasing hot or cold intensity.

In yet another example, computer 54 may command air flow in the cabin of the vehicle to be altered to minimize tension. In one example, cabin windows may be lowered to permit air from outside the vehicle to blow into the cabin. In another example, computer 54 may command pressurized air to be blown onto specific locations of the occupant with varying amounts of pressure, volume, and temperature.

In yet another example, computer 54 may command one or more characteristics of lighting in the vehicle to change to minimize tension. Various characteristics of lighting including location, color, wavelength, intensity, and duration of lighting.

In still yet another example, computer 54 may use music to minimize tension. Specifically, computer 54 may over time monitor how various music types influence tension in the occupant. As a result, computer 54 may determine that various music types minimize tension and play those types of music when tension is found to be high in the occupant.

In another example, computer 54 may engage various scents to be deployed to the cabin of the vehicle. The scents may be tied to known aroma therapies which are believed to minimize tension when applied to an occupant.

In still yet another example, computer 54 may provide commands to the occupant regarding suggested movements to minimize tension. In one illustrative example, computer 54 may detect increased tension and provide commands to the occupant to perform one or more stretching routines to minimize tension.

An energize mode may use sensor data collected by the electronics system 16 to determine an energy level of an occupant. In one example, computer 54 may use several inputs to determine the occupant's energy level. These inputs include: vehicle-based measures, behavioral measures, and physiological measures. Vehicle-based measures include counting a number of deviations from desired lane position and monitoring for changes in movement of a steering wheel and pressure on an accelerator pedal or brake pedal that deviate significantly from previously monitored normal use. Behavioral measures may be monitored through a camera in the cabin and include, for example, yawning, eye closure, eye blinking, and head position. Physiological measures include correlations between ECG signal, Electromyogram (EMG), eletrooculogram (EoG), and EEG may be used to determine drowsiness or low energy level of the occupant.

In one illustrative scenario, computer 54 may determine that an occupant has low energy. As a result, computer 54 may ask the occupant if the occupant wants to increase sensed energy through use of one or more features. In another example, computer 54 may detect decreased energy and automatically engage one or more features to increase the occupant's energy based on the occupant's location or schedule.

In one example, computer 54 via output 56 command massage to be provided by the vehicle seat. Various characteristics of massage may be varied by computer 54 to maximize energy of the occupant such as frequency, intensity, location, and patterns of application to the occupant.

In another example, computer 54 may command application of heat or cooling to the occupant using the vehicle seat and or the vehicle heating and cooling systems to maximize energy of the occupant. Various characteristics of heating and cooling include location of application, temperatures applied, duration, and patterns of application to the occupant. Patterns of application may include alternating hot and cold or slowly increasing hot or cold intensity.

In yet another example, computer 54 may command air flow in the cabin of the vehicle to be altered to maximize energy of the occupant. In one example, cabin windows may be lowered to permit air from outside the vehicle to blow into the cabin. In another example, computer 54 may command pressurized air to be blown onto specific locations of the occupant with varying amounts of pressure, volume, and temperature.

In yet another example, computer 54 may command one or more characteristics of lighting in the vehicle to change to maximize energy of the occupant. Various characteristics of lighting including location, color, wavelength, intensity, and duration of lighting.

In still yet another example, computer 54 may use music to maximize energy of the occupant. Specifically, computer 54 may over time monitor how various music types influence energy level in the occupant. As a result, computer 54 may determine that various music types maximize energy of the occupant and play those types of music when energy level is found to be low in the occupant.

In another example, computer 54 may engage various scents to be deployed to the cabin of the vehicle. The scents may be tied to known aroma therapies which are believed to maximize energy of the occupant when applied to an occupant.

In still yet another example, computer 54 may provide commands to the occupant regarding suggested movements to maximize energy of the occupant. In one illustrative example, computer 54 may detect decreased energy and provide commands to the occupant to perform one or more stretching routines to maximize energy.

An arrival coach mode may use sensor data collected by the electronics system 16 to determine what state of mind the occupant should be at for a specific location or time of day. In one example, electronics system 16 may use Global Positioning System (GPS) data to determine a location of a vehicle and automatically engage one or more of the above mentioned modes so that the occupant is in the appropriate state of mind for the location. In one scenario, the electronics system 16 may determine the vehicle is approaching the occupant's home at the end of the day and that the occupant has high tension. As a result, computer 54 may engage the tension relief mode to minimize tension of the occupant. In another example, electronics system 16 may determine from an occupant's calendar that a work meeting is coming up shortly and the occupant's energy level is low. As a result, computer 54 may engage the energize mode to cause the occupant's energy level to increase in preparation for attending the meeting.

In one example, specific locations and meeting types may be programmed by the occupant for use with the arrival coach mode. In another example, the computer 54 may automatically determine through various factors that certain locations lead to increase tension and other locations lead to decreased tension. As a result, computer 54 may attempt to automatically raise the energy level of the occupant when entering high tension locations and decrease tension of the occupant when entering low tension locations.

Occupant capacity for operating the vehicle may be maximized according to several exemplary modes. Those modes include a driver-capability assessment mode, a behavior-coach mode, a check-in on mode, a time to see doctor mode, an attack alert mode, an attach-coach mode, and a right responder mode.

A driver-capability assessment mode may use sensor data collected by electronics system 16 to determine if the driver's capability to operate the vehicle is impaired due to overload, fatigue, drowsiness, stress, and alcohol or drug impairment. As a result, computer 54 may command via output 56 various equipment in the vehicle to communicate to the driver that their capability is impaired. Computer 54 may also take command of the vehicle to slow the vehicles speed or call for assistance.

A behavior-coach mode may use sensor data collected by electronics system 16 to determine an impact of the occupant's behavior of their capacity to operate the vehicle. As an example, computer 54 may log an incoming phone call followed by a spike in heart rate because the occupant was distracted by the phone call and surprised by changing road conditions. Thus, computer 54 may remind the occupant that various activities have caused distraction before.

A check-in on mode may use sensor data collected by electronics system 16 to determine that the occupant is operating at full capacity. In one example, computer 54 may communicate sensor data via output 56 to a remote person showing the remote person that the occupant is operating at a sufficient capacity. In this example, the occupant may be an elderly occupant the remote person may be a family member.

A time-to-see-doctor mode may use sensor data collected by electronics system 16 to determine that sensed data is indicative that a visit to the doctor is warranted. As an example, the computer 54 may determine that the occupant's blood pressure has been sufficiently high for several days. As a result, computer 54 may via output 56 communicate a suggestion to the occupant to visit with their doctor.

An attack alert mode may use sensor data collected by electronics system 16 to determine that the occupant is suffering from a medical attack such as a heart attack. As a result, computer 54 may command via output 56 that medical personnel or a family member contacted. Computer 54 may also cause the vehicle to be slowed and stopped and the hazard lights to be turned on.

An attach-coach mode may use sensor data collected by electronics system 16 to determine that the occupant is suffering from a medical attack such as a heart attack. As a result, computer 54 may communicate instructions via output 56 to the occupant which causes the occupant to respond to the attack in an optimal way. In one example, computer 54 may communicate to the occupant the need to slow down, pull over, and call for assistance.

A right responder mode may use sensor data collected by electronics system 16 to determine that the occupant's biometric data at the time of and after an accident. The occupant's actual biometric data may then be communicated by electronics system 16 to first responders so that the first responders are better prepared to treat the occupant. In another illustrative example, the electronics system 16 may store the occupant's biometric data over time. Once an accident occurs, the electronics system 16 may send both the historical biometric data and the biometric data from and after the accident to the first responders. In this example, the first responders are able to determine what biometric data is related to the accident rather than typical of the occupant. In yet another example, electronics system 16 gathers known medical data about the occupant and sends the known medical data to first responders along with the biometric data from the crash. In this example, first responders may be notified of an allergy or other medical information relevant to the occupant.

The occupant's emotional well being may be maximized according to several exemplary modes. Those modes include an alter-environment mode, a stress-mapper mode, a task-manager mode, an emotional-geotagging mode, and a mood-optimized playlist mode.

An alter-environment mode may use sensor data collected by electronics system 16 to change the environment of the occupant to maximize emotional well being. In one example, computer 54 may analyze collected sensor data to determine that a change in sound emitted from the vehicle's sound system would improve the emotional well being of the occupant.

A stress-mapper mode may use sensor data collected by electronics system 16 as well as other data collected by the vehicle to determine whether geographical locations and/or routes caused increased stress. As a result, computer 54 may be able to correlate specific locations, traffic patterns, and routes with increased stress and recommend alternatives to minimize stress.

A task-manager mode may use sensor data collected by electronics system 16, other data available from vehicle systems, and data provided by smart devices to determine an optimal arrangement of tasks to be completed. As a result, computer 54 may via output 56 suggest changes to the occupant's schedule, route, media, and phone to maximize productivity while minimizing stress.

An emotional-geotagging mode may use sensor data collected by electronics system 16 and other data, such as location data, provided by the vehicle to tie location with emotional state. In addition, the computer 54 may combine emotional data with communications received and recorded by the vehicle along with location. As a result, computer 54 may learn that various factors which influence the emotional state of the occupant.

A mood-optimized playlist mode may use sensor data collected by electronics system 16 to change the music playlist provided by the sound system of the vehicle. Computer 54 may map emotional state with songs played to determine a response which organizes songs to provide a therapy which minimizes stress. Computer 54 may monitor sensor data to confirm that the mood-optimized playlist is having the intended function and make changes in response to the sensor data obtained.

An occupant's health may be maximized according to several exemplary modes. Those modes include a health-metric gathering mode, a health-metric tracking mode, a health-metric sharing mode, a workout-optimizer mode, a destination-prep mode, and a posture coach mode.

A health-metric gathering mode may use sensor data collected by electronics system 16 to gather and store various health metrics like heart rate, blood pressure, and respiration rate. As a result, computer 54 may provide upon request stored or real-time health metrics about the occupant.

A health-metric tracking mode may use sensor data collected by electronics system 16 to track changes in health metrics over time by storing processed sensor data in memory 542 of computer 54 or communicating processed sensor data to a party remote from vehicle seat. As a result, health metrics may be viewed over a period of time.

A health-metric sharing mode may use sensor data collected by electronics system 16 to provide health metrics which may be shared intermittently or continuously with a third party. Computer 54 may via output 56 communicate to a doctor, for example, heart rate information collected over a period of time.

A workout-optimizer mode may use sensor data collected by electronics system 16 to determine a workout routine which arranges a workout to accomplish the occupants goals. In one example, the occupant may wish to maximize muscle gain and computer 54 may arrange a workout which maximizes muscle gain by sensing which muscles will benefit most from a workout and providing exercises which accomplish this result. Computer 54 also may analyze pre-workout sensor data and post-workout sensor data to determine if the workout was optimal. Computer 54 may also optimize an occupant's workout to maximize the occupant's metabolism.

A destination-prep mode may use sensor data collected by electronics system 16 and other data provided to computer 54 to prepare the occupant for their arrival at their destination. As a result, the occupant may be able to take steps which allow them to be in the best position to arrive at their destination. As an example, computer 54 may determine from sensor data that the occupant is drowsy and suggest that coffee or food may be beneficial prior to arrival so that the occupant is awake.

A posture coach mode may use sensor data collected by electronics system 16 to determine that the occupant's current posture while sitting on vehicle seat 10 could be improved. Computer 54 may provide via output 56 suggestions to the occupant of how to improve the occupant's posture along with benefits that may come from changes in posture such as improved mood, increased blood flow to certain areas of the back, reduced back pain, and better visibility.

Usability and value of the vehicle may be maximized according to several exemplary modes. Those modes include an identification mode and an insight mode.

An identification mode may use sensor data collected by electronics system 16 to determine an occupant's identity. Computer 54 may examine various signals collected by electronics system 16 and use features of those signals to identify an occupant. In one example, time domain features may be extracted from the ECG signal and used to identify an occupant. In one example, computer 54 may collect data such as heart rate and breath rate and associate that data with a specific occupant based on features of the ECG signal currently being received by computer 54. As a result, the data collected by the computer 54 is associated and stored with the appropriate user. As a result, biometric history stored and transferred to a healthcare provider or first responder is confirmed to belong to the occupant.

In another example, certain vehicle features may be enabled or disabled based on the identity of the occupant. As an example, the computer 54 may detect that an owner's son who is sixteen is driving the vehicle. The computer 54 may also detect that an occupant other than one of the parents is in the passenger seat. As a result, the computer 54 may not allow the vehicle to be started due to pre-programmed restrictions put in place by the owner.

An insight mode may be used by the occupant to determine trends and changes in health, comfort, and state of mind over time. In one example, the electronics system 16 may determine an initial tension level of the occupant each day as the occupant returns home after work. Over time, the computer 54 may show that the tension relief, mode, for example, has reduced a tension level of the occupant over time so that the occupant is more relaxed when the occupant arrives at home. The computer 54 may communicate this information to the occupant via an in-vehicle display, an application used on a smart phone, tablet, or mobile computing device, or via a web browser. As a result, the occupant is able to see the changes over time caused by the electronics system 16.

Electronics system 16 includes ECG sensor system 18, oximetry sensor system 20, and control system 22 as shown in FIG. 8. Electronics system 16 may also include another occupancy sensor system that is configured to sense when an occupant has entered and existed vehicle seat 10. In one example, the occupancy sensor system includes a pressure switch which is biased to an open position and is moved to a closed position when an occupant sits on the vehicle seat. The pressure switch may be coupled to an input 543 of computer 54 (see FIG. 15) to cause oximetry sensor system 20 to initiate and perform a calibration cycle. While a pressure switch is discussed, any other suitable alternative may be used.

As discussed previously, ECG sensor system 18 includes first and second ECG sensor 24, 26, ECG mat 28, and ECG unit 30 as shown in FIG. 8. In one illustrative example, first and second ECG receivers 24, 26 are Plessey EPIC™ Ultra High Impedance Sensors (PS25102). ECG receivers 24, 26 are capacitance based receivers. ECG mat 28 is a conductive mat or any other suitable alternative. ECG unit 30 includes, for example, a Plessey Control and Interface Box (PS25001A) and a driven right leg circuit coupled to the Control and Interface Box.

In another illustrative embodiment, ECG sensor 34 is coupled to a seat cushion 36 and positioned to lie below trim 38 which extends around seat cushion 36 as shown in FIG. 16. ECG sensor 34 is configured to provide means for detecting electrical signals in occupant 50 through trim 38, first, second, and Nth clothing layers 41, 42, and 43N as shown in FIG. 16. In one example, trim 38 is cloth trim. However trim 38 may also be leather trim or any other suitable material. In this example, first clothing layer 41 is a shirt made of cotton. Second clothing layer 42 is an undershirt made from cotton. Nth clothing layer 43N may be a dress coat made from wool or any other suitable alternative. Nth clothing layer 43N may be one layer or may be additional layers.

In another illustrative embodiment, oximetry sensors 31, 32 are coupled to a seat cushion 44 included in seat bottom 12 and arranged to lie below trim 46 and extend around seat cushion 44 as shown in FIG. 17. Oximetry sensors 31, 32 are configured to detect oxygen content in an occupant's blood through trim 46, first, second, and Nth clothing layers 51, 52, and 53N as shown in FIG. 17. In one example, trim 46 is cloth. First clothing layer 51 is a pair of pants made from denim. Second clothing layer 52 is a pair of underpants made from cotton. Nth clothing layer 53N may be a pocket included in the pair of pants or any other suitable alternative. Nth clothing layer 53N may be one layer or multiple layers.

In another example, electronics system 16 may further include a thermal sensor system. The thermal sensor system may be coupled to control system 22 and be configured to provide information relating to temperature and humidity distribution around an occupant, information relating to injured areas of an occupant, and information relating to temperature gradients around an occupant.

In the example where information relating to temperature and humidity distribution around the occupant is provided, personalized and automatic adjustments to heating and cooling of the occupant may be provided by computer 54 using the vehicle's HVAC system to target portions of the occupant for treatment. As a result of knowing specific hot and cold spots on the occupant's body, adjustments to heating and cooling of the occupant may occur in real time without occupant direction or control.

In the example where information relating to injured areas of the occupant is provided, increased blood flow to injured muscle areas may indicate to computer 54 the need for cooling in the area to minimize swelling, to decrease support in the are so that pressure is minimized on the damage area, or provide massage to promote increased blood flow to the area. In the example where information relating to temperature gradients around the occupant are provided, cooperation with other anthropometric data may be useful to target responses of the vehicle and vehicle seat.

The thermal sensor system may include a hydrothermal mat that includes heat-sensitive layers or an array of temperature sensors. The hydrothermal mat may be positioned to lie below the trim of the vehicle seat and be configured to sense heat through the trim whether the trim is cloth or leather. The hydrothermal mat would obtain heat information about a back side of the occupant. The thermal sensor system may also include an infrared camera coupled to the vehicle in such a position as to scan the occupant while seated in the vehicle seat. In another example, the infrared camera may be coupled to the vehicle in such a location so as to scan the occupant prior to being seated on the vehicle seat. An interface for providing such a scan and orienting the occupant during the scan may be the Faurecia SMARTFIT® technology.

Automobile sensor systems may be used to sense and monitor vehicle performance, including engine performance and diagnostics, tire pressure and security. Additional interest has developed in using other types of automobile sensor systems to monitor and enhance certain aspects of the end-user automobile driving experience. For example, automobile seat sensor technology has been deployed to enable such systems to identify automobile drivers, provide automobile security, enhance child safety, and the like.

With regard to automobile seat sensor systems, many systems provide limited information regarding (i) environmental and/or physiological parameters of occupants, and (ii) occupant seating environment and/or automobile cabin environment. Furthermore, certain sensors within such systems may be limiting, in that many sensors are cumbersome to integrate into the seating system, and awkward to deploy on the person of the occupant in the seat. For example, certain systems may require that sensors be physically attached to the skin of the occupant in order to detect physiological states or conditions. Other systems require occupants to wear custom-made clothing containing the sensors necessary for physiological detection. Moreover, the physiological datasets produced by conventional sensor systems do not adequately take into consideration the data produced from multiple, and sometimes different, types of sensors that may be part of a seat sensor system.

Accordingly, there is a need in to have a seat sensor system that is flexible to use and is capable of accommodating different kinds of occupants. The seat sensor system should be capable of detecting certain physiological parameters through one or more layers of clothing. The seat sensor system should also combine data produced from multiple sensors to provide more robust occupant physiological measurement.

While certain exemplary embodiments have been presented in the foregoing detailed description, a vast number of variations exist. The example embodiment or embodiments described herein are not intended to limit the scope, applicability, or configuration of the present disclosure in any way. Various changes may be made in the function and arrangement of elements without departing from the scope of the present disclosure and the legal equivalents thereof.

Various other embodiments and various changes and modifications to the disclosed embodiment(s) will become apparent to those skilled in the art. Particularly, otherwise explicitly mentioned, all above described features, alternatives and/or embodiments of the present disclosure can be combined with each other as far as they are not incompatible or mutually exclusive of others. All such other embodiments, changes, and modifications are intended to come within the scope of the appended claims.

The invention claimed is:

1. An occupant support system comprising
   a sensor system configured to obtain occupant data signals associated with physiological characteristics of an occupant of the occupant support system and
   a control system including an output and a computer having a memory and a processor, the output configured to provide at least one of an audial, visual, olfactory, and tactile feedback to the occupant to change at least one of the physiological characteristics of the occupant and increase a physical comfort of the occupant, the memory having trend data indicative of occupant comfort stored therein, and the processor configured to execute instructions stored in the memory and to control the output, wherein the processor is configured to receive inputs including the occupant data signals, determine occupant health data indicative of physiological characteristics of the occupant using the occupant data signals, determine occupant condition improvement instructions using the occupant health data and trend data stored in the memory and predetermined criteria, and activate the output based on the occupant condition improvement instructions to change at least one of the physiological characteristics of the occupant, wherein the processor is further configured to identify the occupant based on at least one of the inputs and the occupant data signals, sense manual changes made to the output by the occupant, associate the manual changes with the occupant health data, and store the occupant health data, the associated manual changes to the activated output, the occupant condition improvement instructions, and data associated with the activated output activated in the memory in an associated occupant profile of the identified occupant, and wherein the processor is further configured to receive supplemental occupant data signals after the output is activated, determine supplemental occupant health data using the supplemental occupant data signals, and compare the occupant health data, the supplemental occupant health data, and the manual changes made to the output to determine if activating the output resulted in a change in the physiological characteristics of the occupant over time and to determine trends in the physiological characteristics of the occupant and store the trends in the occupant profile so that the processor predicts discomfort and makes changes to the occupant condition improvement instructions and output in response.

2. The occupant support system of claim 1, wherein the processor is further configured to activate the output based on the occupant profile of the occupant associated with the identified identity.

3. The occupant support system of claim 1, wherein the processor is further configured to receive supplemental occupant data signals after the output is activated, determine supplemental occupant health data using the supplemental occupant data signals, determine supplemental occupant condition improvement instructions using the data associated with the occupant profile, the supplemental occupant health data, and the predetermined criteria, and activate the output based on the supplemental occupant condition improvement instructions.

4. The occupant support system of claim 1, wherein the processor is further configured to determine supplemental occupant condition improvement instructions using the occupant health data and the supplemental occupant health data and activate the output based on the supplemental occupant condition improvement instructions.

5. The occupant support system of claim 1, wherein the inputs further include vehicle-based measurements and behavioral measurements of the occupant and the processor is configured to determine the occupant condition improvement instructions using the occupant health data, the trend data, the vehicle-based measurements, and the behavioral measurements.

6. The occupant support system of claim 1, wherein the output is configured to instruct a heating, ventilation, and air conditioning system to change at least one of a temperature, a blower speed, and a blower angle.

7. The occupant support system of claim 6, wherein the output is configured to instruct the heating, ventilation, and air conditioning system to provide at least one of localized heating and localized cooling to the occupant.

8. The occupant support system of claim 7, wherein the output is configured to instruct the heating, ventilation, and air conditioning system to change at least one of a heating and cooling to a face of the occupant.

9. The occupant support system of claim 1, wherein the sensor system includes a thermal sensor system configured to provide data indicative of at least one of temperature and humidity distribution around the occupant, injured areas of the occupant, and temperature gradients around the occupant.

10. The occupant support system of claim 9, wherein the thermal sensor system includes at least one of a hydrothermal mat and an infrared camera.

11. The occupant support system of claim 1, wherein the output is configured to instruct a massage system to perform a first massage algorithm.

12. The occupant support system of claim 11, wherein at least one of a frequency, intensity, location, and patterns of application to the occupant of the first massage algorithm is based on the occupant condition improvement instructions.

13. The occupant support system of claim 11, wherein the output is configured to instruct the massage system to perform a second massage algorithm different than the first massage algorithm after the first massage algorithm has started and the second massage algorithm differs from the first massage algorithm in at least one of a frequency, intensity, location, and patterns of application to the occupant.

14. The occupant support system of claim 1, wherein the output is configured to instruct a lighting system to vary at least one of a location, color, wavelength, intensity, and duration of lighting included in the lighting system.

15. The occupant support system of claim 1, wherein the output is configured to instruct a scent system to deploy aroma therapies.

16. The occupant support system of claim 1, wherein the output is configured to instruct a sound system to play one of a plurality of audio recordings at a predetermined volume.

17. The occupant support system of claim 1, wherein the one of a plurality of audio recordings and the predetermined volume are determined based on the occupant condition improvement instructions.

* * * * *